US010414769B2

(12) United States Patent
Treu et al.

(10) Patent No.: US 10,414,769 B2
(45) Date of Patent: Sep. 17, 2019

(54) 5,8-DIMETHYL-9-PHENYL-5,8-DIHYDRO-6H-PYRAZOLO[3,4-H]QUINAZOLIN-2-YL)-(1H-PYRAZOL-3-YL)-AMINES AS IGF-1R/IR INHIBITORS

(71) Applicant: Boehringer Ingelheim International GmbH, Ingelheim am Rhein (DE)

(72) Inventors: Matthias Treu, Vienna (AT); Stephan Karl Zahn, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/572,992

(22) PCT Filed: May 10, 2016

(86) PCT No.: PCT/EP2016/060481
§ 371 (c)(1),
(2) Date: Nov. 9, 2017

(87) PCT Pub. No.: WO2016/180843
PCT Pub. Date: Nov. 17, 2016

(65) Prior Publication Data
US 2018/0141948 A1    May 24, 2018

(30) Foreign Application Priority Data

May 13, 2015  (EP) .................................. 15167553

(51) Int. Cl.
| A61K 31/519 | (2006.01) |
| C07D 487/04 | (2006.01) |
| A61P 37/00 | (2006.01) |
| A61P 31/00 | (2006.01) |
| A61P 29/00 | (2006.01) |
| A61P 35/00 | (2006.01) |

(52) U.S. Cl.
CPC ............ *C07D 487/04* (2013.01); *A61P 29/00* (2018.01); *A61P 31/00* (2018.01); *A61P 35/00* (2018.01); *A61P 37/00* (2018.01)

(58) Field of Classification Search
CPC ............................. A61K 31/519; C07D 487/04
USPC .......................................... 514/267; 544/251
See application file for complete search history.

(56) References Cited

FOREIGN PATENT DOCUMENTS

| WO | 2012010704 A1 | 1/2012 |
| WO | 2013110585 A1 | 8/2013 |
| WO | WO 16/180843 | * 11/2016 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report PCT/EP2016/060481 dated Jun. 29, 2016.
Sanderson, M.P. et al. "BI 885578, a Novel IGF1R/INSR Tyrosine Kinase Inhibitor with Pharmacokinetic Properties That Dissociate Antitumor Efficacy and Perturbation of Glucose Homeostasis" (2015) Molecular Cancer Therapeutics, vol. 14, No. 12, 2762-2772.

* cited by examiner

*Primary Examiner* — Douglas M Willis
(74) *Attorney, Agent, or Firm* — Atabak R. Royaee

(57) ABSTRACT

The present invention encompasses compounds of formula (I)

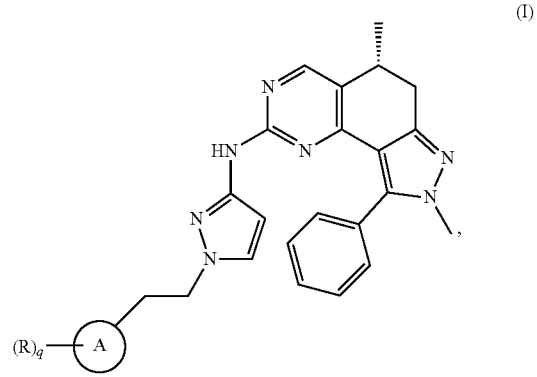

wherein the groups A, R and q are defined in claim 1, their use as inhibitors of IGF-1R, pharmaceutical compositions which contain compounds of this kind and their use as medicaments, especially as agents for treatment and/or prevention of oncological diseases.

18 Claims, No Drawings

5,8-DIMETHYL-9-PHENYL-5,8-DIHYDRO-6H-PYRAZOLO[3,4-H]QUINAZOLIN-2-YL)-(1H-PYRAZOL-3-YL)-AMINES AS IGF-1R/IR INHIBITORS

The present invention relates to new 5,8-dimethyl-9-phenyl-5,8-dihydro-6H-pyrazolo[3,4-h]quinazolin-2-yl)-(1H-pyrazol-3-yl)-amines and derivatives of formula (I)

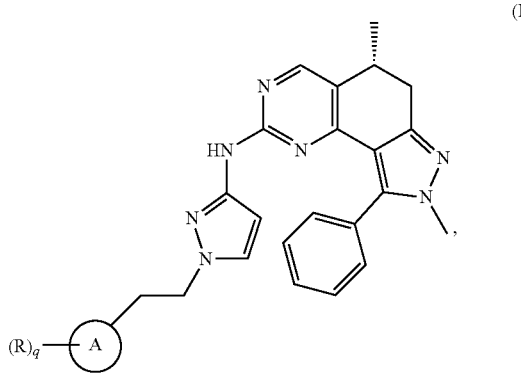

wherein the groups A, R and q have the meanings given in the claims and specification, their use as inhibitors of IGF-1R/IR, pharmaceutical compositions which contain compounds of this kind and their use as medicaments, especially as agents for treatment and/or prevention of oncological diseases.

BACKGROUND OF THE INVENTION

WO 2005/037843 describes partially saturated quinazolines anellated with heteroaryls as kinase inhibitors.

WO 2012/010704 and WO 2013/110585 describe 5,8-dihydro-6H-pyrazolo[3,4-h]quinazolines as IGF-1R/IR inhibitors.

The aim of the present invention is to provide new compounds which can be used for the prevention and/or treatment of diseases characterised by excessive or abnormal cell proliferation. The compounds (I) according to the invention are characterised by a powerful inhibitory effect on the kinase activity of the IGF-1 receptor (IGF-1R) and insulin receptor (IR) and a high efficacy against tumour cells, e.g. EWING'S sarcoma, glioblastoma, colorectal cancer etc., which is mediated through the inhibition of phosphorylation of the receptor. In addition to the inhibitory effect and cell activity, compounds (I) show good solubility. In summary, the profile of compounds (I) according to the invention for the first time combines high inhibitory effect on the target IGF-1R, high cellular potency on cancer cells, fine-tuned DMPK properties optimized to prevent or minimize adverse effects immanent to the treatment with IGF1-R/IR inhibitors, e.g. hyperglycemia, and good selectivity over other kinases of the human kinome. Compounds (I) according to the invention are neither anticipated by structurally-related prior art compounds disclosed in patent applications cited hereinbefore or elsewhere nor is there teaching or suggestion which would have guided the skilled person. The inventors had to take every endeavor to provide compounds (I) with these balanced properties.

The insulin-like growth factor (IGF) and insulin signalling network is a highly conserved and essential pathway involved in biological processes including growth, metabolism and homeostasis. In addition, deregulated signalling via this network can enhance tumorigenesis and metastasis of certain cancers.

The ligands IGF-1, IGF-2 and insulin are highly homologous and activate specific hetero or homodimers of the IGF-1R and IR. Following ligand binding, the IGF-1R and IR undergo autophosphorylation mediated via the receptor tyrosine kinase domains. The phosphorylated receptors activate the canonical Ras-Raf-MEK-ERK1/2 and PI3K-PDK1-Akt intracellular signalling cascades, which leads to oncogenic cell proliferation, growth and survival. In addition, activation of the IR by insulin stimulates the uptake of glucose and storage of glycogen in metabolic tissues such as the liver, adipose and muscle.

Published research articles as well as medical and epidemiological investigations have identified a strong correlation between expression of the IGF-1R and IR and ligands for these receptors in tumor development and progression. Intrinsic dependence can be mediated via dysregulated gene or protein expression, function or genetic alteration of the IGF-1R, IR, IGF ligands (IGF1 and IGF2), insulin or other key pathway components including IGF-binding proteins (IGFBPs), IGF2R, IGFBP proteases and/or micro RNAs and RNA binding proteins.

Developing a small molecule competitive inhibitor of the ATP-binding pocket of the IGF-1R and IR as a means of blocking growth and survival signalling cascades in cancer is therefore desirable. The anticipated clinical benefit of blocking such an interaction would be to reduce tumor proliferation, growth and survival and potentially sensitize tumors to cytotoxic agents or targeted therapies.

DETAILED DESCRIPTION OF THE INVENTION

It has now been found that, surprisingly, compounds of formula (I) wherein the groups A, R and q have the meanings given hereinafter act as inhibitors of IGF-1R/IR which are involved in controlling cell proliferation. Thus, the compounds according to the invention may be used for example for the treatment of diseases characterised by excessive or abnormal cell proliferation.

The present invention therefore relates to a compound of formula (I)

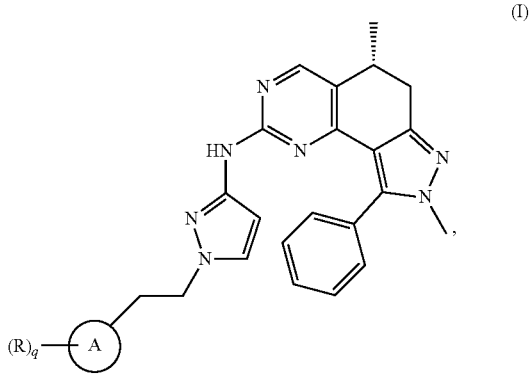

wherein
--
A is a 5-7 membered nitrogen-containing heterocyclyl optionally substituted with one oxo group;
--
each R is $C_{1-6}$alkyl, optionally substituted by one or more, identical or different $R^{b1}$ and/or $R^{c1}$;
  each $R^{b1}$ is independently selected from among —$OR^{c1}$ and —$C(O)OR^{c1}$;
  each $R^{c1}$ independently of one another is selected from among hydrogen, $C_{1-6}$alkyl, 3-10 membered heterocyclyl and $C_{1-6}$alkyl substituted with a 3-10 membered heterocyclyl;
--
q denotes the number 0, 1 or 2;
or a salt thereof.

In one aspect the invention relates to a compound of formula (I), wherein
A is selected from among pyrrolidinyl, piperidinyl, piperazinyl, morpholinyl, homopiperidinyl, homopiperazinyl and homomorpholinyl, all optionally substituted with one oxo group;
or a salt thereof.

In another aspect the invention relates to a compound of formula (I), wherein
A is selected from among piperazinyl, morpholinyl and piperazinonyl;
or a salt thereof.

In another aspect the invention relates to a compound of formula (I), wherein
A is selected from among piperazin-1-yl, morpholin-4-yl and 2-oxo-piperazin-4-yl;
or a salt thereof.

In another aspect the invention relates to a compound of formula (I), wherein
A is piperazin-1-yl;
or a salt thereof.

In another aspect the invention relates to a compound of formula (I), wherein
A is piperazin-1-yl;
one of the q substituents R, if present, is located in the 4-position of the piperazin-1-yl;
or a salt thereof.

In another aspect the invention relates to a compound of formula (I), wherein
each R is $C_{1-4}$alkyl, optionally substituted with hydroxy or methoxy;
or a salt thereof.

In another aspect the invention relates to a compound of formula (I), wherein
each R is selected from among methyl and ethyl and each of said methyl and ethyl is substituted with a substituent selected from among —$C(O)OR^{c1}$ and 5-6 membered heterocyclyl;
  $R^{c1}$ is selected from among 5-6 membered heterocyclyl and methyl substituted with 5-6 membered heterocyclyl;
or a salt thereof.

In another aspect the invention relates to a compound of formula (I), wherein
each 5-6 membered heterocyclyl in R is independently selected from among pyrrolidinyl, tetrahydrofuryl and tetrahydropyranyl;
or a salt thereof.

In another aspect the invention relates to a compound of formula (I), wherein
q is 1;
or a salt thereof.

In another aspect the invention relates to a compound of formula (I), wherein
R binds to a ring nitrogen atom of ring A;
or a salt thereof.

In another aspect the invention relates to a compound of formula (I), wherein
q is 0;
or a salt thereof.

In another aspect the invention relates to a compound of formula (I) selected from among

I-1

I-2

-continued
I-3
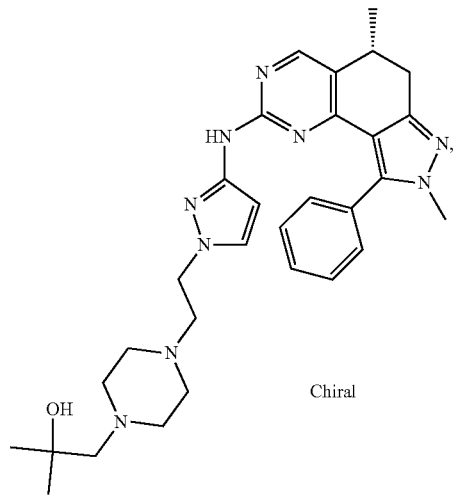
Chiral
I-4
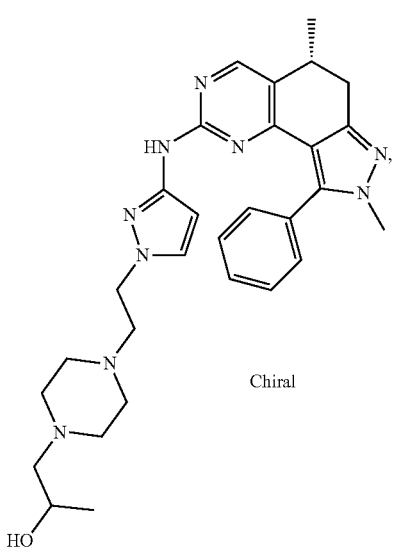
Chiral
I-5
-continued
I-6
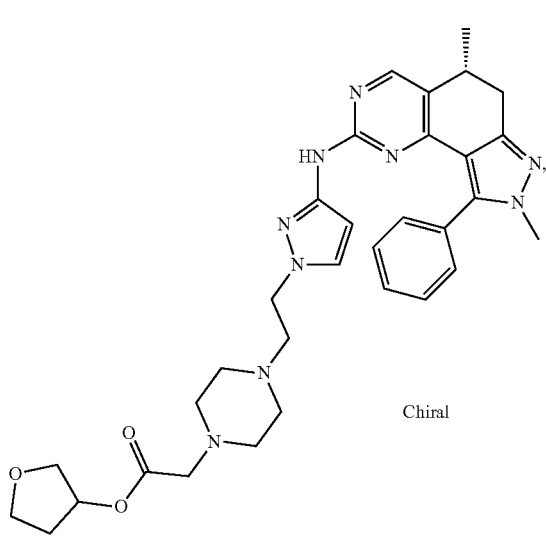
Chiral
I-7
Chiral
I-8
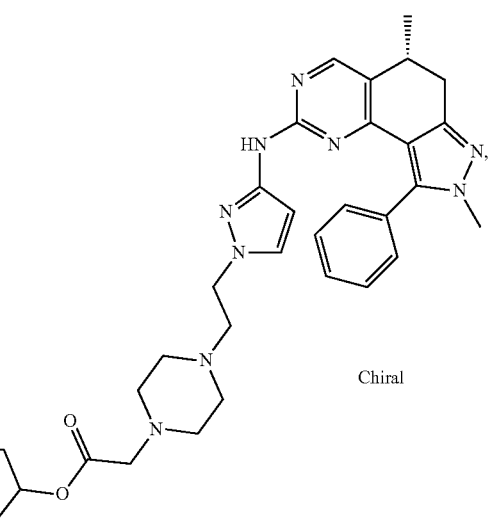
Chiral

I-9

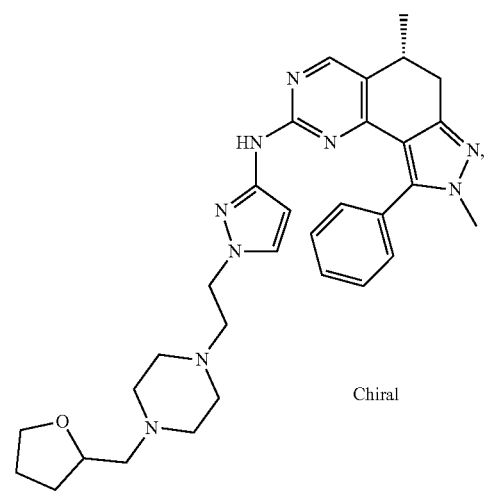

I-12

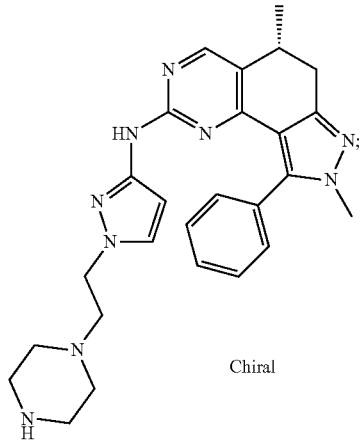

or a salt thereof.

All the above-mentioned structural aspects are preferred embodiments of compounds (I). The structural aspects relating to different molecular parts of the compounds (I) according to the invention may be permutated with one another as desired in combinations so as to obtain preferred compounds (I). Each combination represents and defines individual embodiments or generic subsets of compounds according to the invention.

In a further aspect the invention also relates to the synthetic intermediate C or its salts, racemate or geometric isomers, which can be used as intermediate in the synthesis of compounds of formula (I):

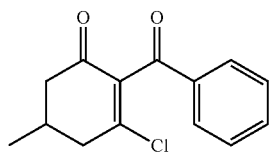 [SMILES: CC1CC(=O)C(C(=O)c2ccccc2)=C(Cl)C1]

C

In a further aspect the invention also relates to the use of synthetic intermediate C or its salts, racemate or geometric isomers in the synthesis of compounds (I).

In a further aspect the invention also relates to the synthetic intermediate D or its salts, racemate or geometric isomers, which can be used as intermediate in the synthesis of compounds of formula (I):

I-10

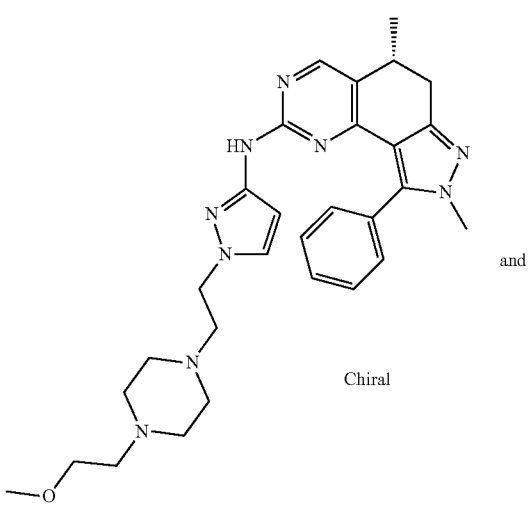

I-11 and

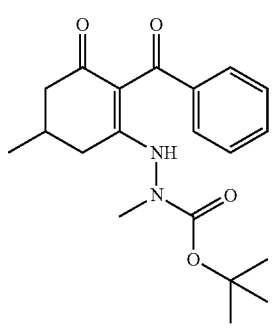 [SMILES: CC1CC(=O)C(C(=O)c2ccccc2)=C(NN(C)C(=O)OC(C)(C)C)C1]

D

In a further aspect the invention also relates to the use of synthetic intermediate D or its salts, racemate or geometric isomers in the synthesis of compounds (I).

In a further aspect the invention also relates to the synthetic intermediate (R)-E or its salts, racemate, enantiomer or geometric isomers, which can be used as intermediate in the synthesis of compounds of formula (I):

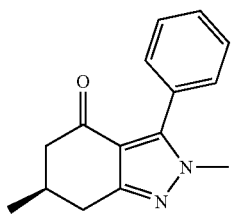 [SMILES: C[C@H]1CC(=O)c2c(nn(C)c2-c2ccccc2)C1]

(R)-E

In a further aspect the invention also relates to the use of synthetic intermediate (R)-E or its salts, racemate, enantiomer or geometric isomers in the synthesis of compounds (I).

In a further aspect the invention also relates to the synthetic intermediate (R)-F or its salts, racemate, enantiomer or geometric isomers, which can be used as intermediate in the synthesis of compounds of formula (I):

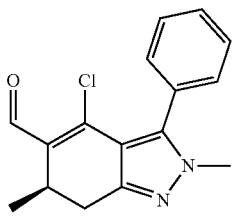 [SMILES: C[C@@H]1Cc2nn(C)c(-c3ccccc3)c2C(Cl)=C1C=O]

(R)-F

In a further aspect the invention also relates to the use of synthetic intermediate (R)-F or its salts, racemate, enantiomer or geometric isomers in the synthesis of compounds (I).

In a further aspect the invention also relates to the synthetic intermediate L (structure see scheme 3) or its salts, which can be used as intermediate in the synthesis of compounds of formula (I).

In a further aspect the invention also relates to the use of synthetic intermediate L (structure see scheme 3) or its salts in the synthesis of compounds (I).

In a further aspect the invention also relates to the synthetic intermediate N (structure see scheme 3 and table 4) or its salts, which can be used as intermediate in the synthesis of compounds of formula (I).

In a further aspect the invention also relates to the use of synthetic intermediate N (structure see scheme 3 and table 4) or its salts in the synthesis of compounds (I).

In a further aspect the invention also relates to the synthetic intermediate P (structure see scheme 3 and table 5) or its salts, which can be used as intermediate in the synthesis of compounds of formula (I).

In a further aspect the invention also relates to the use of synthetic intermediate P (structure see scheme 3 and table 5) or its salts in the synthesis of compounds (I).

In a further aspect the invention also relates to the synthetic intermediates M (structure see scheme 3), wherein groups A, R and q are as hereinbefore defined, or their salts, which can be used as intermediate in the synthesis of compounds of formula (I).

In a further aspect the invention also relates to the use of synthetic intermediate M (structure see scheme 3), wherein groups A, R and q are as hereinbefore defined, or their salts in the synthesis of compounds (I).

In a further aspect the invention also relates to the synthetic intermediates O (structure see scheme 3), wherein groups A, R and q are as hereinbefore defined, or their salts, which can be used as intermediate in the synthesis of compounds of formula (I).

In a further aspect the invention also relates to the use of synthetic intermediate O (structure see scheme 3), wherein groups A, R and q are as hereinbefore defined, or their salts in the synthesis of compounds (I).

In a further aspect the invention also relates to the synthetic intermediates Q (structure see scheme 3), wherein groups A, R and q are as hereinbefore defined, or their salts, which can be used as intermediate in the synthesis of compounds of formula (I).

In a further aspect the invention also relates to the use of synthetic intermediates Q (structure see scheme 3), wherein groups A, R and q are as hereinbefore defined, or their salts in the synthesis of compounds (I).

The definitions of groups A, R and q in intermediates M, O and Q correspond to those as given for compound (I) above. Preferred intermediates M, O and Q are those which lead to preferred compounds (I) according to the invention, i.e. preferred embodiments of M. O and Q have structural aspects as defined above for compounds (I). These structural aspects may be permutated with one another as desired so as to obtain preferred intermediates M, O and Q. Each combination represents and defines individual embodiments or generic subsets of intermediates M, O and Q.

Preferred intermediates M are M-1, M-2 and M-3 (table 3) and the salts thereof.

Preferred intermediates O are O-1, O-2 and O-3 (table 4) and the salts thereof.

Preferred intermediates Q are Q-1, Q-2 and Q-3 (table 5) and the salts thereof.

The present invention further relates to hydrates, solvates, polymorphs, metabolites, derivatives, isomers and prodrugs of a compound of formula (I).

The present invention further relates to a pharmaceutically acceptable salt of a compound of formula (I).

The present invention further relates to a pharmaceutically acceptable salt of a compound of formula (I) with anorganic or organic acids or bases.

The present invention is directed to compounds of formula (I) which are useful in the prevention and/or treatment of a disease and/or condition wherein the inhibition of IGF-1R and/or IR is of therapeutic benefit, including but not limited to the treatment and/or prevention of cancer.

In another aspect the invention relates to a compound of formula (I)—or a pharmaceutically acceptable salt thereof—as a medicament.

In another aspect the invention relates to a compound of formula (I)—or a pharmaceutically acceptable salt thereof—for use in a method for treatment of the human or animal body.

In another aspect the invention relates to a compound of formula (I) or—or a pharmaceutically acceptable salt thereof—for use in the treatment and/or prevention of a disease and/or condition wherein the inhibition of IGF-1R and/or IR is of therapeutic benefit.

In another aspect the invention relates to a compound of formula (I)—or a pharmaceutically acceptable salt thereof—for use in the treatment and/or prevention of cancer, infections, inflammations and autoimmune diseases.

In another aspect the invention relates to a compound of formula (I)—or a pharmaceutically acceptable salt thereof—for use in a method for treatment and/or prevention of cancer, infections, inflammations and autoimmune diseases in the human and animal body.

In another aspect the invention relates to the use of a compound of formula (I) or—or a pharmaceutically acceptable salt thereof—for preparing a pharmaceutical composition for the treatment and/or prevention of cancer, infections, inflammations and autoimmune diseases.

In another aspect the invention relates to a compound of formula (I)—or a pharmaceutically acceptable salt thereof—for use in the treatment and/or prevention of cancer.

In another aspect the invention relates to the use of a compound of formula (I) or—or a pharmaceutically acceptable salt thereof—for preparing a pharmaceutical composition for the treatment and/or prevention of cancer.

In another aspect the invention relates to a compound of formula (I)—or a pharmaceutically acceptable salt thereof—for use in a method for treatment and/or prevention of cancer in the human or animal body.

In another aspect the invention relates to a compound of formula (I)—or a pharmaceutically acceptable salt thereof—for use in the treatment and/or prevention of cancers intrinsically dependent on oncogenic signalling via the IGF-1R and/or IR.

In another aspect the invention relates to the use of a compound of formula (I)—or a pharmaceutically acceptable salt thereof—for preparing a pharmaceutical composition for the treatment and/or prevention of cancers intrinsically dependent on oncogenic signalling via the IGF-1R and/or IR.

In another aspect the invention relates to a compound of formula (I)—or a pharmaceutically acceptable salt thereof—for use in the treatment and/or prevention of soft tissue and bone sarcomas, prostate cancer, breast cancer, bladder cancer, adrenal gland cancer, liver cancer, lung cancer, colon cancer and ovary cancer.

In another aspect the invention relates to the use of a compound of formula (I)—or a pharmaceutically acceptable salt thereof—for preparing a pharmaceutical composition for the treatment and/or prevention of soft tissue and bone sarcomas, prostate cancer, breast cancer, bladder cancer, adrenal gland cancer, liver cancer, lung cancer, colon cancer and ovary cancer.

In another aspect the invention relates to a method for the treatment and/or prevention of a disease and/or condition wherein the inhibition of IGF-1R and/or IR is of therapeutic benefit comprising administering a therapeutically effective amount of a compound of formula (I)—or a pharmaceutically acceptable salt thereof—to a human being.

In another aspect the invention relates to a method for the treatment and/or prevention of cancer comprising administering a therapeutically effective amount of a compound of formula (I)—or a pharmaceutically acceptable salt thereof—to a human being.

In another aspect the invention relates to a pharmaceutical composition comprising at least one compound of formula (I)—or a pharmaceutically acceptable salt thereof—and a pharmaceutically acceptable carrier.

In another aspect the invention relates to a pharmaceutical preparation comprising a compound of formula (I)—or a pharmaceutically acceptable salt thereof—and at least one other cytostatic or cytotoxic active substance, different from formula (I).

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example H₃C—, H₃C—CH₂—, H₃C—CH₂—CH₂—, H₃C—CH(CH₃)—. H₃C—CH₂—CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

Further examples of alkyl are methyl (Me; —CH₃), ethyl (Et; —CH₂CH₃), 1-propyl (n-propyl; n-Pr; —CH₂CH₂CH₃), 2-propyl (i-Pr; iso-propyl; —CH(CH₃)₂), 1-butyl (n-butyl; n-Bu; —CH₂CH₂CH₂CH₃), 2-methyl-1-propyl (iso-butyl; i-Bu; —CH₂CH(CH₃)₂), 2-butyl (sec-butyl; sec-Bu; —CH(CH₃)CH₂CH₃), 2-methyl-2-propyl (tert-butyl; t-Bu; —C(CH₃)₃), 1-pentyl (n-pentyl; —CH₂CH₂CH₂CH₂CH₃), 2-pentyl (—CH(CH₃)CH₂CH₂CH₃), 3-pentyl (—CH(CH₂CH₃)₂), 3-methyl-1-butyl (iso-pentyl; —CH₂CH₂CH(CH₃)₂), 2-methyl-2-butyl (—C(CH₃)₂CH₂CH₃), 3-methyl-2-butyl (—CH(CH₃)CH(CH₃)₂), 2,2-dimethyl-1-propyl (neo-pentyl; —CH₂C(CH₃)₃), 2-methyl-1-butyl (—CH₂CH(CH₃)CH₂CH₃), 1-hexyl (n-hexyl; —CH₂CH₂CH₂CH₂CH₂CH₃), 2-hexyl (—CH(CH₃)CH₂CH₂CH₂CH₃), 3-hexyl (—CH ($CH_2CH_3$)($CH_2CH_2CH_3$)), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$) etc.

By the terms propyl, butyl, pentyl, hexyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CH(CH(CH_3))_2$)— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene. The above definition for alkylene also applies if alkylene is part of another (combined) group such as for example in HO—$C_{x-y}$alkyleneamino or $H_2N$—$C_{x-y}$alkyleneoxy.

By heteroatoms are meant oxygen, nitrogen and sulphur atoms.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies if aryl is part of another (combined) group as for example in arylamino, aryloxy or arylalkyl.

If the free valency of an aryl is saturated, then an aromatic group is obtained.

Heterocyclyl denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

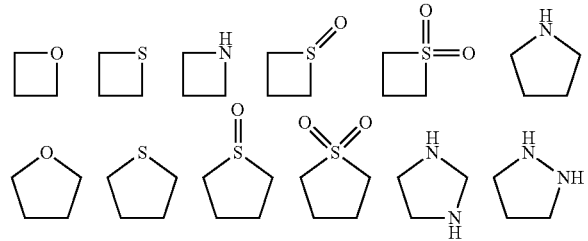

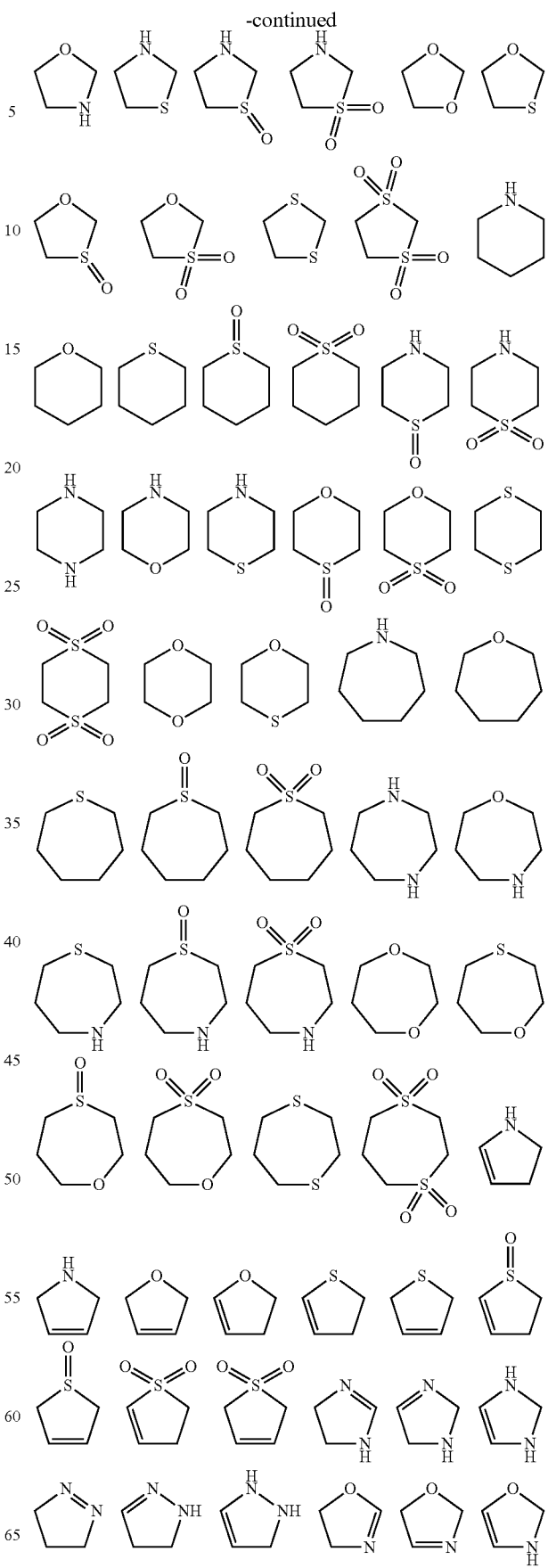

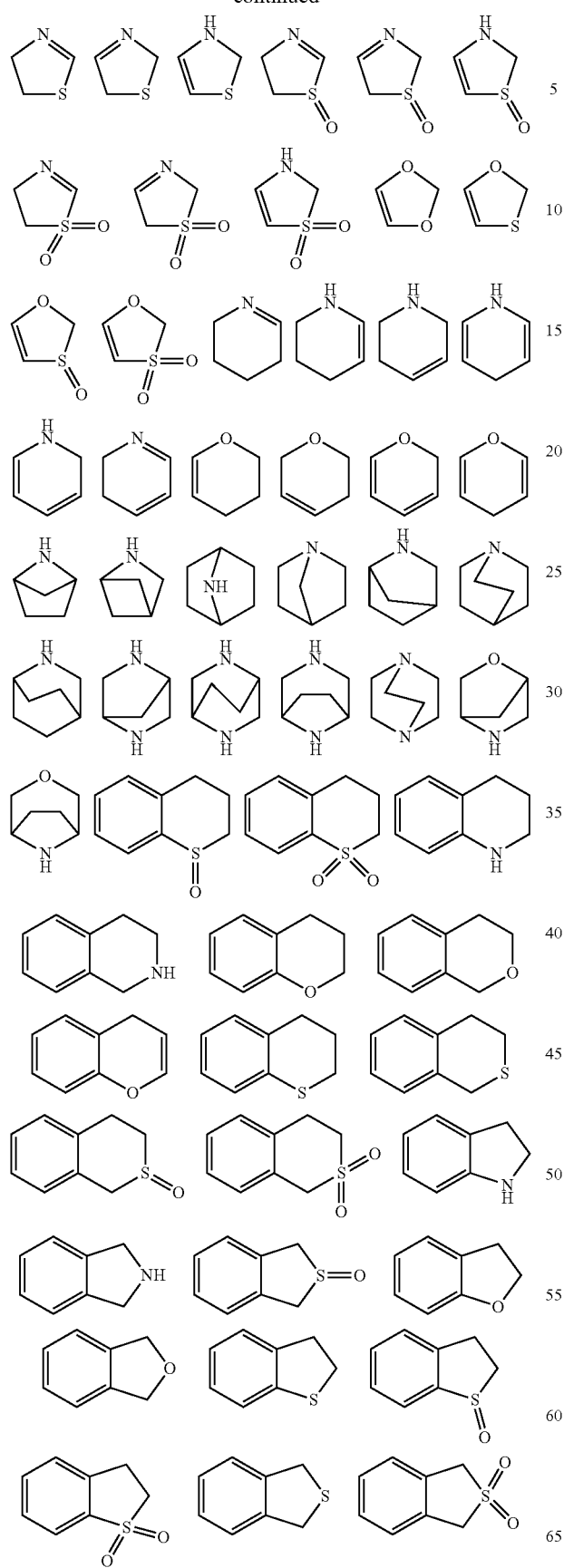
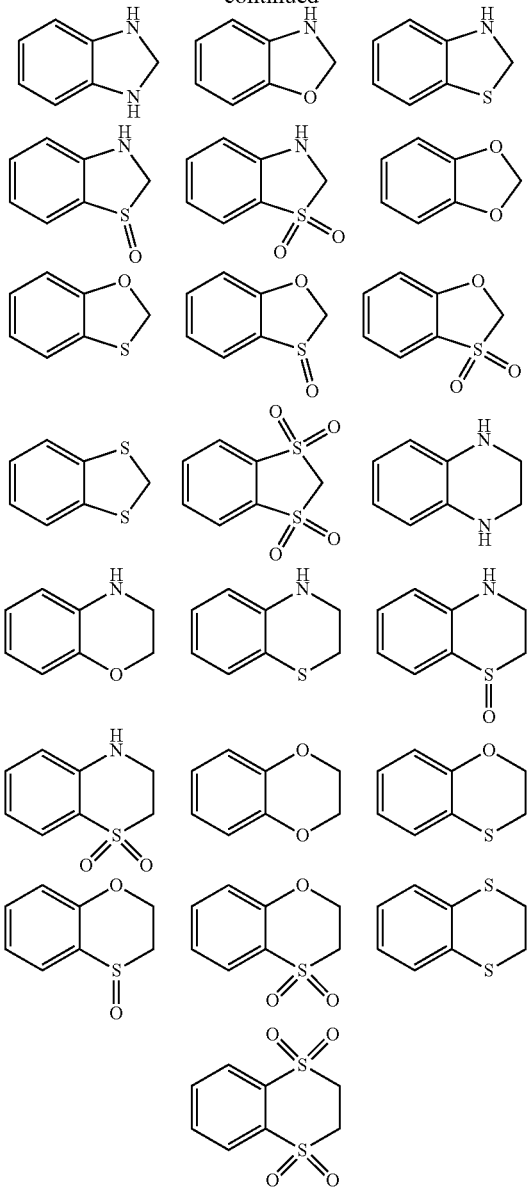

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, pyrrolidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, wherein the bivalent substituent =O may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O only) of a ring system.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from ammonia, L-arginine, betaine, benethamine, benzathine, calcium hydroxide, choline, deanol, diethanolamine (2,2'-iminobis (ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol), tromethamine, zinc hydroxide, acetic acid, 2,2-dichloro acetic acid, adipic acid, alginic acid, ascorbic acid (L), L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid (capric acid), dodecylsulfuric acid, ethane-1,2-disulfonic acid, ethanesulfonic acid, 2-hydroxyethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycine, glycolic acid, hexanoic acid (caproic acid), hippuric acid, hydrobromic acid, hydrochloric acid, isobutyric acid, DL-lactic acid, lactobionic acid, lauric acid, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, octanoic acid (caprylic acid), oleic acid, orotic acid, oxalic acid, palmitic acid, pamoic acid (embonic acid), phosphoric acid, propionic acid, (−)-L-pyroglutamic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

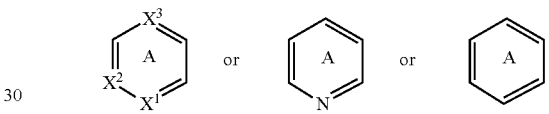

the letter A has the function of a ring designation in order to make it easier, for example, to indicate the attachment of the ring in question to other rings.

Groups or substituents are frequently selected from among a number of alternative groups/substituents with a corresponding group designation (e.g. $R^a$, $R^b$ etc.). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| | |
|---|---|
| Ac | acetyl |
| AcCN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| CBZ | benzyloxycarbonyl |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DEAD | diethyl azodicarboxylate |
| DIPEA | N-ethyl-N,N-diisopropylamine (Hünig's base) |

-continued

| | |
|---|---|
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1,1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| PE | petroleum ether |
| Ph | phenyl |
| Pr | propyl |
| Py | pyridine |
| rac | racemic |
| red. | reduction |
| Rf ($R_f$) | retention factor |
| RP | reversed phase |
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:

PREPARATION OF COMPOUNDS ACCORDING TO THE INVENTION

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 µm, 50×150 mm or SunFire™ Prep C18 OBD™ 5 µm, 30×50 mm or XBridge™ Prep C18, OBD™ 10 µm, 50×150 mm or XBridge™ Prep C018, OBD™ 5 µm, 30×150 mm or XBridge™ Prep C18, OBD™ 5 µm, 30×50 mm) and YMC (names: Actus-Triart Prep C18, 5 µm, 20×50 mm).

Different gradients of $H_2O$/acetonitrile are used to elute the compounds, while for Agilent systems 5% acidic modifier (20 mL HCOOH to 1 L $H_2O$/acetonitrile (1:1)) is added to the water (acidic conditions). For Gilson systems the water is added 0.1% HCOOH.

For the chromatography under basic conditions for Agilent systems $H_2O$/acetonitrile gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO_3$ solution (158 g in 1 L $H_2O$) and 2 mL $NH_3$ (28% in $H_2O$) are replenished to 1 L with $H_2O$.

The analytical HPLC (reaction control) of intermediate and final compounds is carried out using columns made by Waters (names: Atlantis dC 182.1×50 mm, 3 µM, XBridge™ C18, 2.5 µm, 2.1×20 mm, XBridge™ XP C18 2.1×30 mm, 2.5. µ, Sunfire 2.1×50 mm, 5µ), Supelco (names: Ascentis Express C18 30×2.1 mm, 2.7 µM) or Agilent (names: Zorbax SB C8 3.5 µm, 80 Å, 50×2.1 mm). The analytical equipment is also equipped with a mass detector in each case.

HPLC-Mass Spectroscopy/UV-Spectrometry

The retention times/MS-ESI$^+$ for characterizing the example compounds according to the invention are produced using an HPLC-MS apparatus (high performance liquid chromatography with mass detector). Compounds that elute at the injection peak are given the retention time $t_{Ret.}$=0.00.

| HPLC-methods | |
|---|---|
| Method A | |
| HPLC | Shimadzu Prominence Series |
| MS | Shimadzu LCMS-2010EV system |
| MSD signal settings | Scan pos 100-1000 |
| column | Waters (Part No. 186001291) Atlantis dC182.1 × 50 mm, 3 µm |

| HPLC-methods | |
|---|---|
| eluent | |
| A | water + 0.1% HCOOH |
| B | acetonitrile + 0.1% HCOOH (HPLC grade) |
| detection | |
| signal | UV 215 nm |
| spectrum | range: 210-420 nm; step: 1 nm |
| injection | 3 μL |
| flow | 1 mL/min |
| column temp. | 40° C. |
| pump gradient | 0.00 min    5% B |
| | 0.00-2.50 min    5% → 100% B |
| | 2.50-2.70 min    100% B |
| | 2.70-2.71 min    100% → 5% B |

Method B

| | |
|---|---|
| HPLC | Shimadzu Prominence Series |
| MS | Shimadzu LCMS-2010EV system |
| MSD signal settings | Scan pos 100-1000 |
| column | Supelco (Part No. 53802-U) Supelco Ascentis Express C18 30 × 2.1 mm, 2.7 μm |
| eluent | |
| A | water + 0.1% HCOOH |
| B | acetonitrile + 0.1% HCOOH (HPLC grade) |
| Detection signal | UV 215 nm |
| spectrum | range: 220-420 nm; step: 1 nm |
| injection | 3 μL |
| flow | 1 mL/min |
| column temp. | 40° C. |
| pump gradient | 0.00 min    5% B |
| | 0.00-1.50 min    5% → 100% B |
| | 1.50-1.60 min    100% B |
| | 1.60-1.61 min    100% → 5% B |

Method C

| | |
|---|---|
| HPLC | Agilent 1100 Series |
| MS | Agilent LC/MSD SL |
| MSD signal settings | Positive and negative<br>Mass range: 120-900 m/z<br>Fragmentor: 120<br>Gain EMV: 1, Threshold: 150, Stepsize: 0.2 |
| UV detection | 315 nm<br>Bandwidth: 170 nm<br>Reference: off<br>Range: 230-400 nm, Range step: 1.00 nm<br>Peakwidth: <0.01 min, Slit: 1 nm |
| column | Waters, Xbridge C18, 2.5 μm, 2.1 × 20 mm, Part. No. 186003201 |
| eluent | A: 20 mM $NH_4HCO_3/NH_3$ pH 9<br>B: acetonitrile HPLC grade |
| injection | 5 μm |
| flow | 1.00 mL/min |
| column temp. | 60° C. |
| pump gradient | 0.00 min    10% B |
| | 0.00-1.50 min    10% → 95% B |
| | 1.50-2.00 min    95% B |
| | 2.00-2.10 min    95% → 10% B |

Method D

| | |
|---|---|
| HPLC | Agilent 1100 Series |
| MS | 1200 Series LC/MSD (API-ES + 3000 V, Quadrupol, G6140A) |
| MSD signal settings | Scan pos 150-750 |
| UV detection | UV 254/214/230 nm (bandwidth 8, reference off)<br>range: 190-450 nm; step: 4.0 nm |
| column | Agilent Zorbax SB, C8, 3.5 μm, 80 Å, 50 × 2.1 mm column, Part. No.: 871700-906 |
| eluent | A: water + 0.1% formic acid<br>B: acetonitrile (HPLC grade) + 0.1% formic acid |
| injection | 1.5 μL |
| flow | 1.1 mL/min |
| column temp. | 45° C. |
| pump gradient | 0.0-1.75 min    15% to 95% B |
| | 1.75-1.9 min    95% B |
| | 1.9-1.92 min    95% to 15% B |
| | 1.92-2.1 min    15% B |

Method E

| | |
|---|---|
| HPLC | Agilent 1260 Series |
| MS | 1260 Series LC/MSD (API-ES + 3000 V, Quadrupol, G6130B) |
| MSD signal settings | Scan pos/neg 100-800 |
| UV detection | UV 254/230 nm (bandwidth 8, reference off)<br>range: 190-400 nm; step: 4.0 nm |
| column | Waters XBridge XP C18 2.1 × 30 mm, 2.5μ |
| eluent | A: water (5 mM $NH_4HCO_3$, 19 mM $NH_3$)<br>B: acetonitrile (HPLC grade) |
| injection | 0.5 μL |
| flow | 1.4 mL/min |
| column temp. | 45° C. |
| pump gradient | 0.00 min    5% B |
| | 0.00-1.00 min    5% to 100% B |
| | 1.00-1.37 min    100% B |
| | 1.37-1.40 min    100% to 5% B |

Method F

| | |
|---|---|
| HPLC | Agilent 1100 Series |
| MS | 1100 Series LC/MSD (API-ES + 3000 V, Quadrupol, G1956B) |
| MSD signal settings | Scan pos/neg 150-750 |
| UV detection | UV 254/230 nm (bandwidth 8, reference off)<br>range: 190-450 nm; step: 4.0 nm |
| column | Waters Sunfire, 2.1 × 50 mm, 5μ<br>Bestellnummer: 186002539 |
| eluent | A: water (0.2% HCOOH)<br>B: acetonitrile (HPLC grade) |
| injection | 2 μL |
| flow | 1.2 mLI/min |
| column temp. | 45° C. |
| pump gradient | 0.00 min    5% B |
| | 0.00-1.50 min    5% to 95% B |
| | 1.50-1.51 min    95% to 100% B |
| | 1.51-1.56 min    100% B |
| | 1.56-1.57 min    100% to 5% B |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known prior art compounds or methods described herein. Substances described in the literature are prepared according to the published methods of synthesis.

General Reaction Schemes and Summary of the Synthesis Route

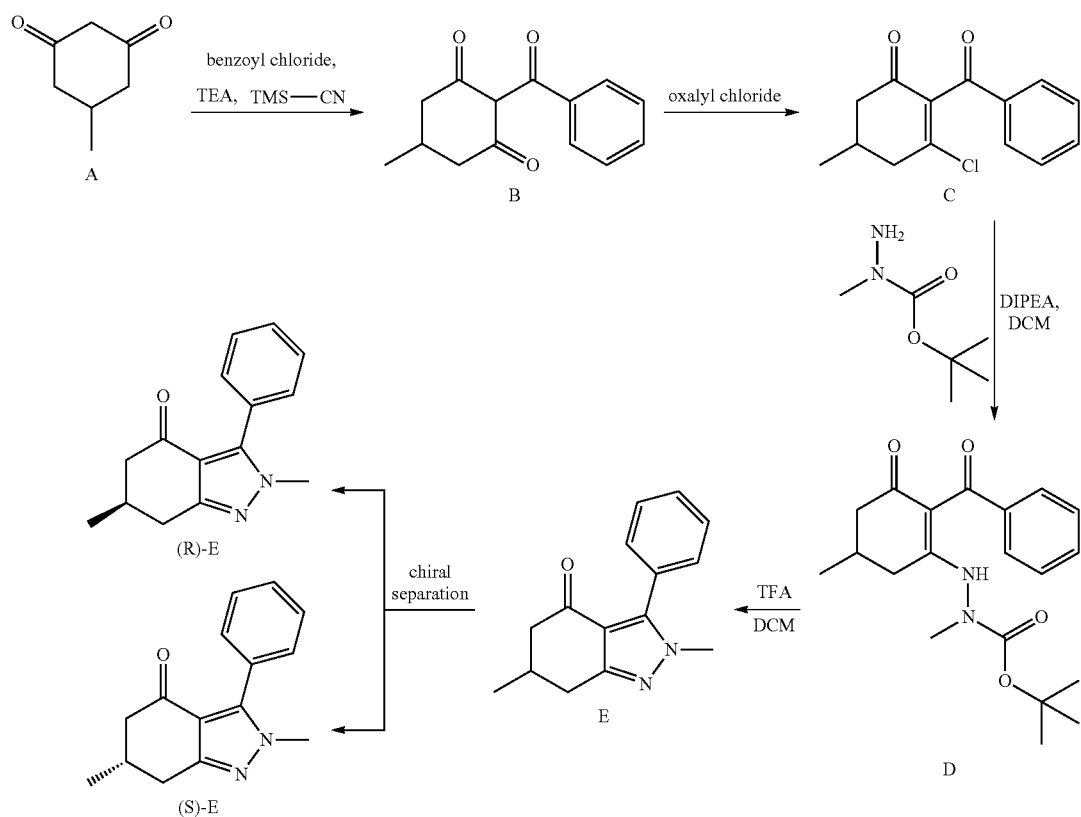

Starting with diketone A this starting material is acylated to form intermediate B in a 2-step process. After chlorination to form the activated MICHAEL acceptor C a stepwise process involving a cyclisation yields the central racemic intermediate E.

Chiral chromatography enables the separation of the enantiomers of E. The (R)-enantiomer (R)-E is the desired intermediate that serves as the central starting material for the next steps shown in Scheme 2. Alternatively, the further synthetic steps can also be performed with the racemic mixture E and chiral separation can take place at any later step as desired.

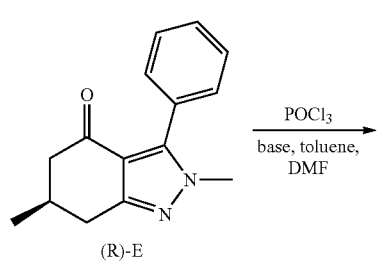

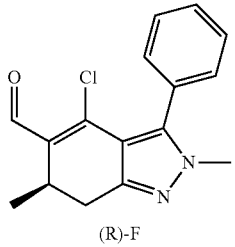

(R)-E is converted/activated via chloroformylation to (R)-F which can be directly cyclised to the compounds (I) by reaction with respective guanidines P or Q (see scheme 3).

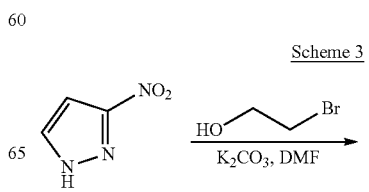

27
-continued
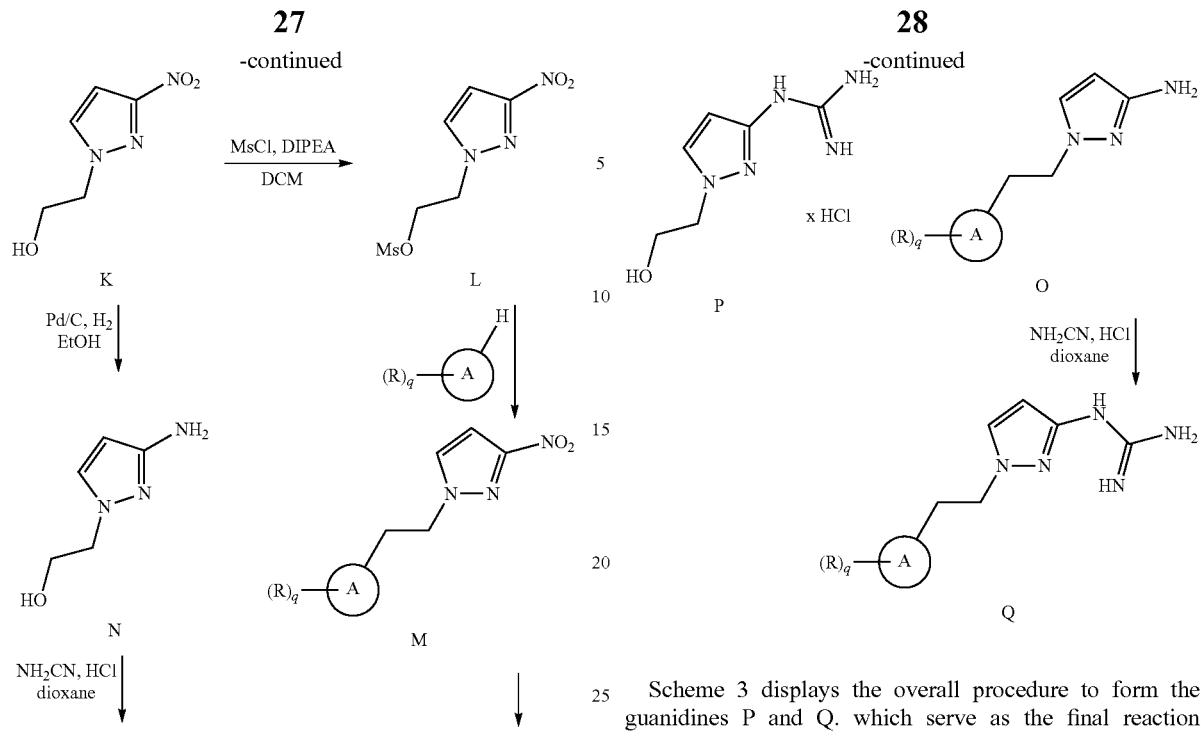
Scheme 3 displays the overall procedure to form the guanidines P and Q. which serve as the final reaction partners for (R)-F.
Scheme 4
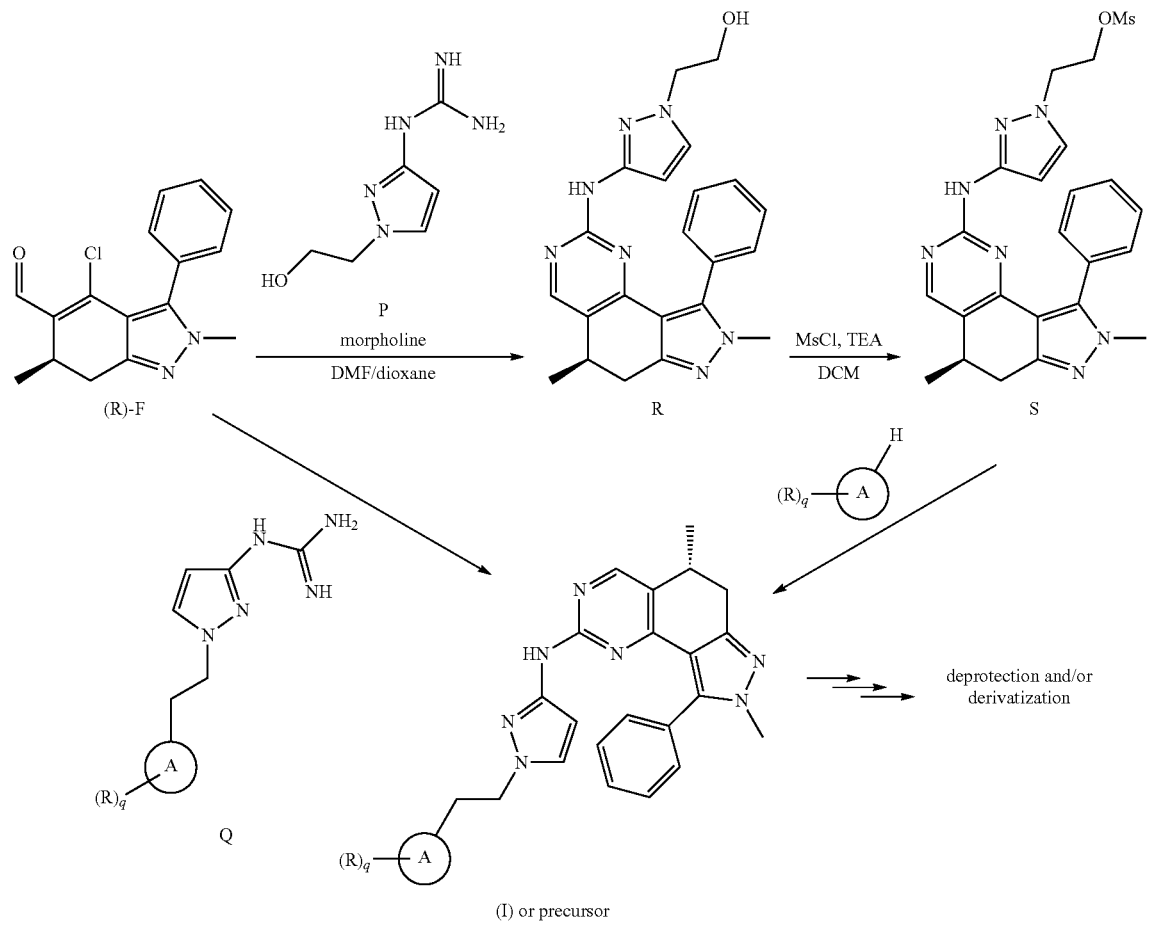

The final compounds (I) can be obtained (scheme 4) by reaction of the pyrazologuanidines P or Q with the precursor molecule (R)-F. If P is used in the cyclisation step the group $(R)_q$-A- has to be introduced in further steps by, e.g., mesylation and nucleophilic substitution. Compounds obtained directly after nucleophilic substitution may optionally obtain their final decoration after further steps of deprotection and/or derivatization.

Synthesis of
2-benzoyl-5-methyl-cyclohexane-1,3-dione
(Intermediate B)

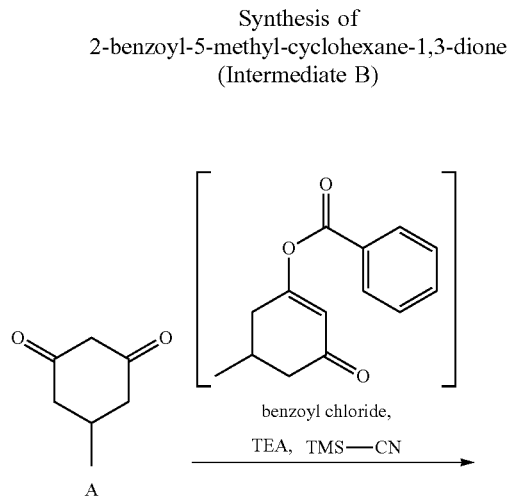

5-Methyl-cyclohexane-1,3-dione (starting material A; 5.0 g, 839.6 mmol, 1 eq.) is dissolved in 25 mL acetonitrile. Subsequently TEA (15 mL, 109 mmol, 2.8 eq.), benzoyl chloride (5.6 g, 39.8 mmol, 1.0 eq) and trimethylsilylcyanide (0.7 mL, 8.9. mmol, 0.22 eq.) are added at rt. The reaction mixture is stirred at 60° C. for 4 h and then at rt overnight.

After neutralization with 2 N HCl (aq.) the mixture is extracted with EtOAc, the combined organic phases are washed with saturated brine and finally dried over sodium sulfate. After removal of the volatile solvent under reduced pressure the crude product B is isolated (7.3 g, 31.7 mmol, 80%) and used for the next step without further purification ($R_f$ (PE:EtOAc 3:1)=0.5).

Synthesis of
2-benzoyl-3-chloro-5-methyl-cyclohex-2-enone
(Intermediate C)

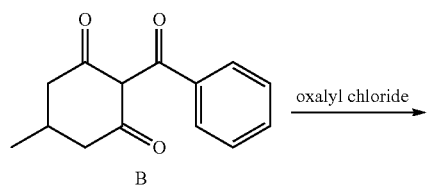

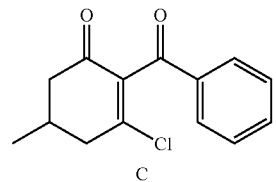

2-benzoyl-5-methyl-cyclohexane-1,3-dione (intermediate B) (7.3 g, 31.7 mmol, 1 eq.) is dissolved in 50 mL oxalyl chloride, a few drops DMF are added and the reaction mixture is to stirred for 3 h. After removal of all volatile components under reduced pressure the residue is dissolved in chloroform and the solution is successively washed with water, saturated sodium bicarbonate solution and water. After the organic phase is dried over sodium sulfate the solvent is removed under reduced pressure to obtain the crude intermediate C (6.3 g, 25.3 mmol, 80%) which is used for the next step without further purification ($R_f$ (PE:EtOAc 3:1)=0.7).

Synthesis of N'-(2-benzoyl-5-methyl-3-oxo-cyclohex-1-enyl)-N-methyl-hydrazinecarboxylic Acid tert-butyl Ester (Intermediate D)

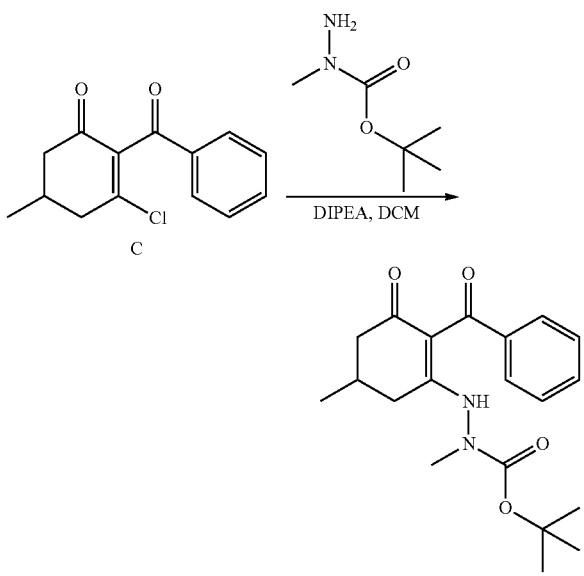

2-benzoyl-3-chloro-5-methyl-cyclohex-2-enone (intermediate C: 6.3 g, 25.53 mmol, 1 eq.) is dissolved in DIPEA (3.3 g, 25.3 mmol, 1 eq.). This solution is added dropwise to a solution of N-methyl-hydrazinecarboxylic acid tert-butyl ester (3.7 g, 25.3 mmol, 1 eq.) dissolved in 20 mL DCM. The reaction mixture is stirred at rt for 48 h and then poured into water. After repeated extraction with DCM the combined organic phases are washed with brine, dried over sodium sulfate and all solvent is removed under reduced pressure to obtain the crude intermediate D (6.8 g, 19.0 mmol, 75%) which is used for the next step without further purification ($R_f$ (PE:EtOAc 3:1)=0.3).

Synthesis of 2,6-dimethyl-3-phenyl-2,5,6,7-tetrahydro-indazol-4-one (Intermediate E)

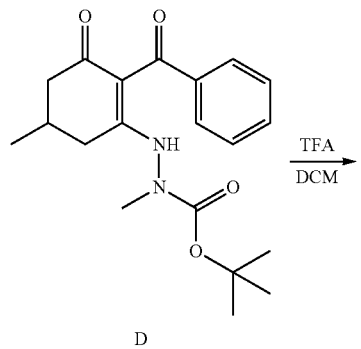

Intermediate D (6.8 g, 19.0 mmol, 1 eq.) is dissolved in a mixture of 15 mL DCM and 30 mL TFA and the reaction mixture is stirred for 3 h rt. After removal of all solvents at reduced pressure the remaining crude product is dissolved in DCM and successively washed with water and brine. After drying over sodium sulfate and evaporation a brown oil is obtained. Purification by normal phase chromatography on silica with petrolether/EtOAc gives 3.6 g (15.0 mmol, 79%) of racemic intermediate E ($R_f$ (PE:EtOAc 3:1)=0.5).

Chiral Separation of Racemic 2,6-dimethyl-3-phenyl-2,5,6,7-tetrahydro-indazol-4-one (Intermediate E)

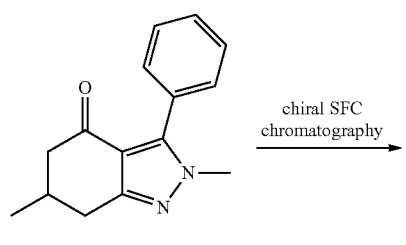

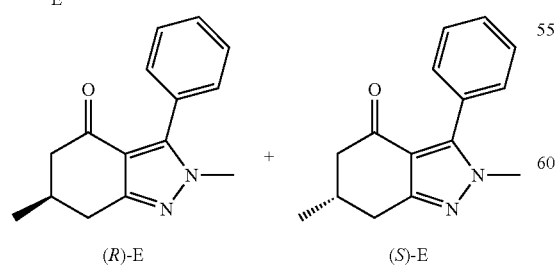

Racemic 2,6-dimethyl-3-phenyl-2,5,6,7-tetrahydro-indazol-4-one (intermediate E) (18 g, 74.9 mmol) is subjected to preparative chiral SFC chromatography to obtain 6.1 g (25.4 mmol, 34%) (R)-2,6-dimethyl-3-phenyl-2,5,6,7-tetrahydro-indazol-4-one (R)-E and 5.8 g (24.1 mmol, 32%) (S)-2,6-dimethyl-3-phenyl-2,5,6,7-tetrahydro-indazol-4-one (S)-E.

Details:
Instrument: Thar 80 preparative SFC;
Column: Chiralpak AD-H, 250×30 mm id. 5 μm;
Mobile phase: A for $CO_2$ and B for MeOH (0.05% $NH_3$ in $H_2O$);
Gradient: B %=30%;
Flow rate: 65 g/min;
System back pressure: 100 bar;
Column temperature: 40° C.;
Wavelength: 220 nm;
Injection amount: 75 mg per injection;
Cycle time: 6 min.

TABLE 1

| # | product | $t_{ret}$ [min] | [M + H]⁺ | HPLC method |
|---|---|---|---|---|
| B | 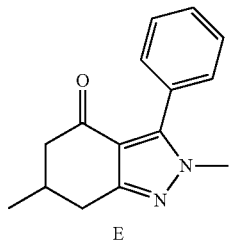 | 0.90 | 231 | D |
| C | | 1.10 | 249/251 | D |
| D | | 1.07 | 359 | D |
| E | | 0.92 | 241 | D |
| (R)-E | | 1.00 | 241 | C |

TABLE 1-continued

| # | product | $t_{ret}$ [min] | $[M + H]^+$ | HPLC method |
|---|---------|-----------------|-------------|-------------|
| (S)-E | 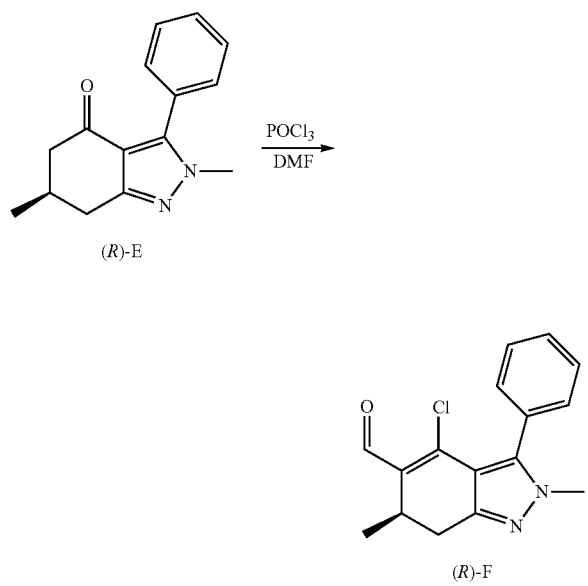 | 1.00 | 241 | C |

Synthesis of (R)-4-chloro-2,6-dimethyl-3-phenyl-6,7-dihydro-2H-indazole-5-carbaldehyde (Intermediate (R)-F)

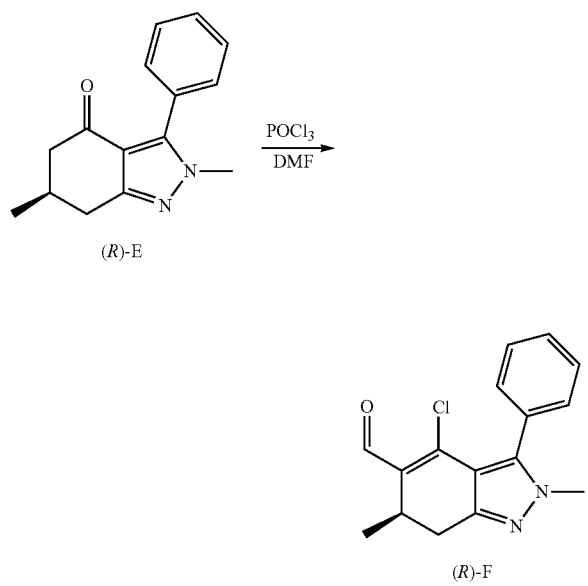

DMF (22 g, 285 mmol, 6.9 eq.) is dissolved in chloroform (300 mL) and cooled to 0° C. POCl$_3$ (20 mL, 218 mmol, 5.3 eq.) is added dropwise at 0° C. and the reaction mixture is stirred at that temperature for 15 min. Then a solution of (R)-2,6-dimethyl-3-phenyl-2,5,6,7-tetrahydro-indazol-4-one (R)-E (10.0 g, 41.2 mmol, 1 eq.) in chloroform (100 mL) is added dropwise at 0° C. The reaction mixture is stirred overnight at rt and is then poured into ice water (1.2 L). The pH is adjusted to pH 8-9 by adding 50% aq. NaOH dropwise. The organic phase is separated and the aqueous phase is extracted twice with chloroform (200 mL). The organic phases are combined, washed with brine and dried over magnesium sulfate. All volatile components are removed under reduced pressure. Then the crude material is dissolved in toluene (3×, each 200 mL) and concentrated under reduced pressure to remove all residual water to yield 14.6 g (40.8 mmol, 99%) of crude product (R)-F that can be used for subsequent reactions without any further purification.

TABLE 2

| # | product | $t_{ret}$ [min] | $[M + H]^+$ | HPLC method |
|---|---------|-----------------|-------------|-------------|
| (R)-F | 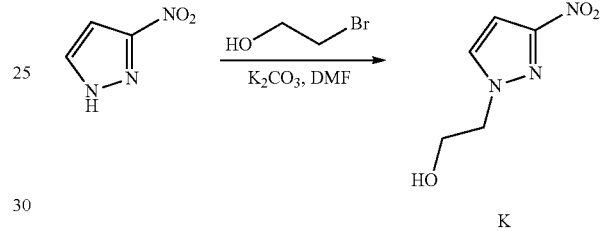 | 0.72 | 287/289 | D |

Synthesis of 2-(3-nitro-1H-pyrazol-1-yl)ethan-1-ol (Intermediate K)

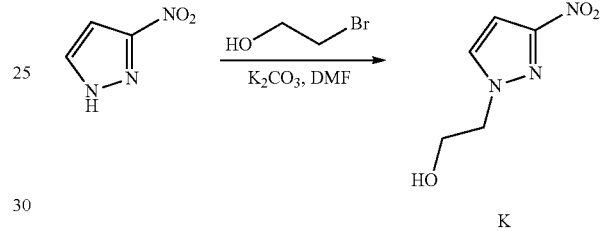

K$_2$CO$_3$ (48.9 g, 353.8 mmol) is added to a solution of 3-nitro-1H-pyrazole (20.0 g, 176.9 mmol) in THF (200 mL) followed by 2-bromo-ethanol (18.8 mL, 265.3 mmol) and the mixture is heated under reflux for 24 h. After cooling, the mixture is partitioned between water (200 mL) and EtOAc (200 mL). The phases are separated and the aqueous phase is extracted with EtOAc (2×200 mL). The combined organic phases are dried (MgSO$_4$), filtered and concentrated in vacuo. The crude residue is purified by trituration from Et$_2$O, the solid is collected by filtration and washed with Et$_2$O, DCM and Et$_2$O again. The filtrate is concentrated in vacuo and is triturated from Et$_2$O. The solids are combined to give the title compound (18.1 g, 64% yield) as an off-white solid.

Synthesis of 1-(2-methoxy-ethyl)$_4$-[2-(3-nitro-1H-pyrazol-1-yl)-ethyl]-piperazine

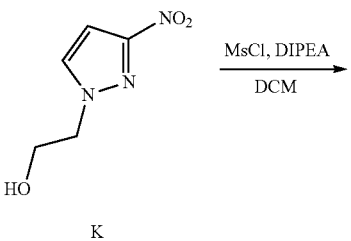

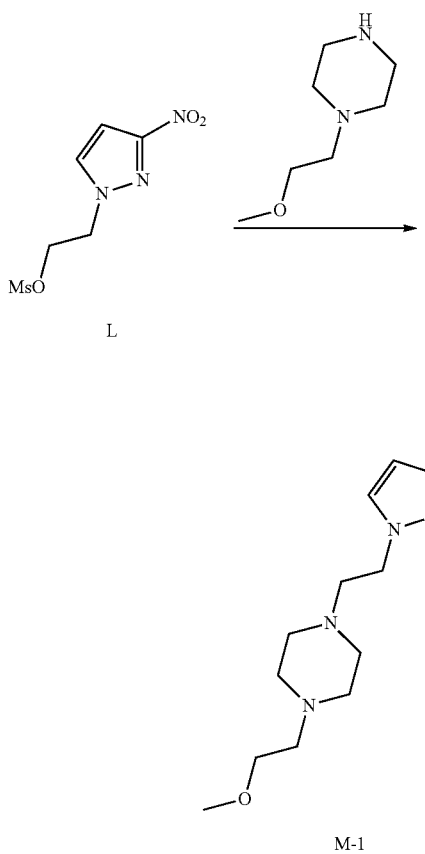

DIPEA (5.0 mL, 30.6 mmol) is added to a solution of 2-(3-nitro-pyrazol-1-yl)-ethanol (intermediate K; 3.0 g, 19.1 mmol) in anhydrous DCM (150 mL) at 0° C. followed by dropwise addition of methanesulfonyl chloride (2.2 mL. 28.6 mmol) and the mixture is stirred at 0° C. for 2 h. Methanesulfonyl chloride (0.5 mL, 6.5 mmol) is added and stirring is continued for 30 min. The mixture is quenched with sat. NaHCO$_3$ and the aqueous phase is extracted with DCM (2×50 mL). The combined organic phases are dried (Na$_2$SO$_4$), filtered and concentrated in vacuo (→intermediate L)

The residue is dissolved in DMF (10 mL), 1-(2-methoxy-ethyl)-piperazine (28.1 mL, 190.9 mmol) is added and the mixture is stirred at rt overnight followed by heating to 80° C. for 2 h. After cooling, the mixture is partitioned between DCM (30 mL) and 1 M NaHCO$_3$ (30 mL). The phases are separated and the aqueous phase is extracted with DCM (2×20 mL). The combined organic phases are dried (Na$_2$SO$_4$), filtered and concentrated in vacuo. The crude residue is purified by column chromatography with DCM/MeOH (100:0-92:8 gradient) as the eluent. The residue is further purified by column chromatography with DCM/MeOH (99:1-95:5 gradient) as the eluent. The residue is dissolved in DCM and washed with water, the organic phase is concentrated in vacuo to give the title compound M-1 (3.2 g, 59%) as a yellow oil.

Intermediates M-2 and M-3 (Table 3) are obtained in an analogous procedure if 1-(2-methoxy-ethyl)-piperazine is replaced by N-methyl-piperazine and morpholine, respectively.

TABLE 3

| # | structure | t$_{ret}$ [min] | [M + H]$^+$ | HPLC method |
|---|---|---|---|---|
| K | 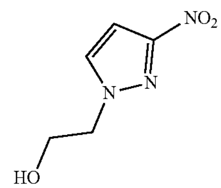 [SMILES: O=[N+]([O-])c1ccn(CCO)n1] | 0.70 | 158 | A |
| M-1 | 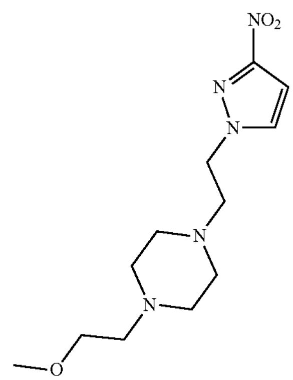 [SMILES: COCCN1CCN(CCn2ccc([N+](=O)[O-])n2)CC1] | 0.16 | 284 | B |
| M-2 | 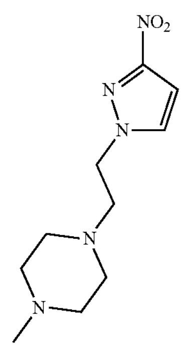 [SMILES: CN1CCN(CCn2ccc([N+](=O)[O-])n2)CC1] | 0.23 | 240 | C |
| M-3 | 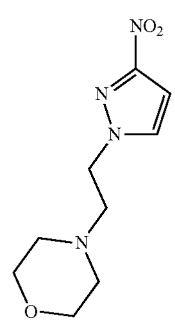 [SMILES: O=[N+]([O-])c1ccn(CCN2CCOCC2)n1] | 0.42 | 227 | B |

Synthesis of 2-(3-amino-1H-pyrazol-1-yl)ethan-1-ol (Intermediate N)

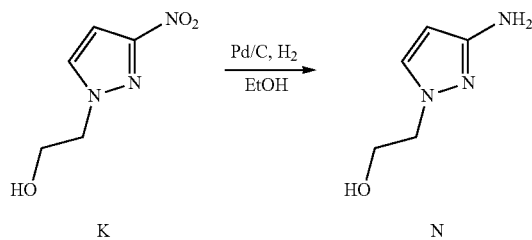

Pd/C (10%; 508 mg, 0.48 mmol) is added to a de-gassed solution of 2-(3-nitro-1H-pyrazol-1-yl)ethan-1-ol (intermediate K; 5.0 g, 31.8 mmol) in EtOH (50 mL) and the mixture is stirred at rt under an atmosphere of hydrogen overnight. The catalyst is removed by filtration through Celite® and washed with EtOH and EtOAc. The filtrate is concentrated in vacuo. The crude residue is dissolved in EtOAc and MeOH and filtered through Celite® for a second time. The filtrate is concentrated in vacuo and azeotroped with heptane to give the title compound N (3.66 g, 91%) as a yellow oil. The aminopyrazoles O-1, O-2 and O-3 can be prepared analogously.

TABLE 4

| # | structure | $t_{ret}$ [min] | $[M + H]^+$ | HPLC method |
|---|---|---|---|---|
| N | 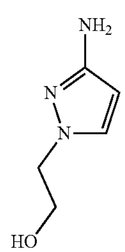 | 0.26 | 129 | A |
| O-1 | 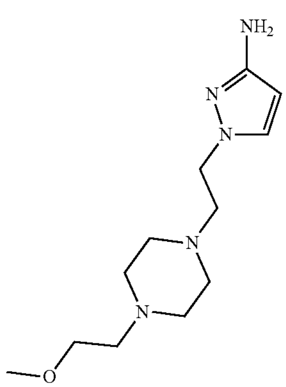 [SMILES: COCCN1CCN(CCn2ccc(N)n2)CC1] | 0.13 | 254 | B |
| O-2 | | n.a. | n.a. | |
| O-3 | | 0.17 | 197 | B |

Synthesis of N—[1-(2-hydroxy-ethyl)-1H-pyrazol-3-yl]-guanidine Hydrochloride (Intermediate P)

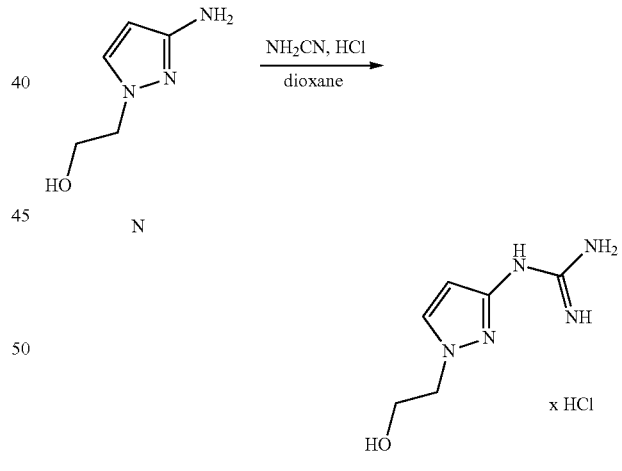

4 M HCl in dioxane (7.2 mL, 29 mmol) is added to a solution of 2-(3-amino-1H-pyrazol-1-yl)ethan-1-ol (intermediate N; 3.66 g, 29 mmol) and cyanamide (1.33 g, 32 mmol) in anhydrous dioxane (20 mL) and the mixture is heated at 80° C. for 3 h. After cooling, the mixture is concentrated in vacuo and azeotroped with heptane to give the title compound (7.38 g, 97%) as a yellow oil.

Guanidine Q-3 can be prepared analogously.

Guanidines with more complex substitution pattern are accessible via the method described by C. E. Stephens, J.

*Med. Chem.* 2001, 1741-1748 and H. Ube, *J. Organomet. Chem.* 2007, 545-using isothioureas:

Synthesis of bis-Cbz-protected Guanidine U-1

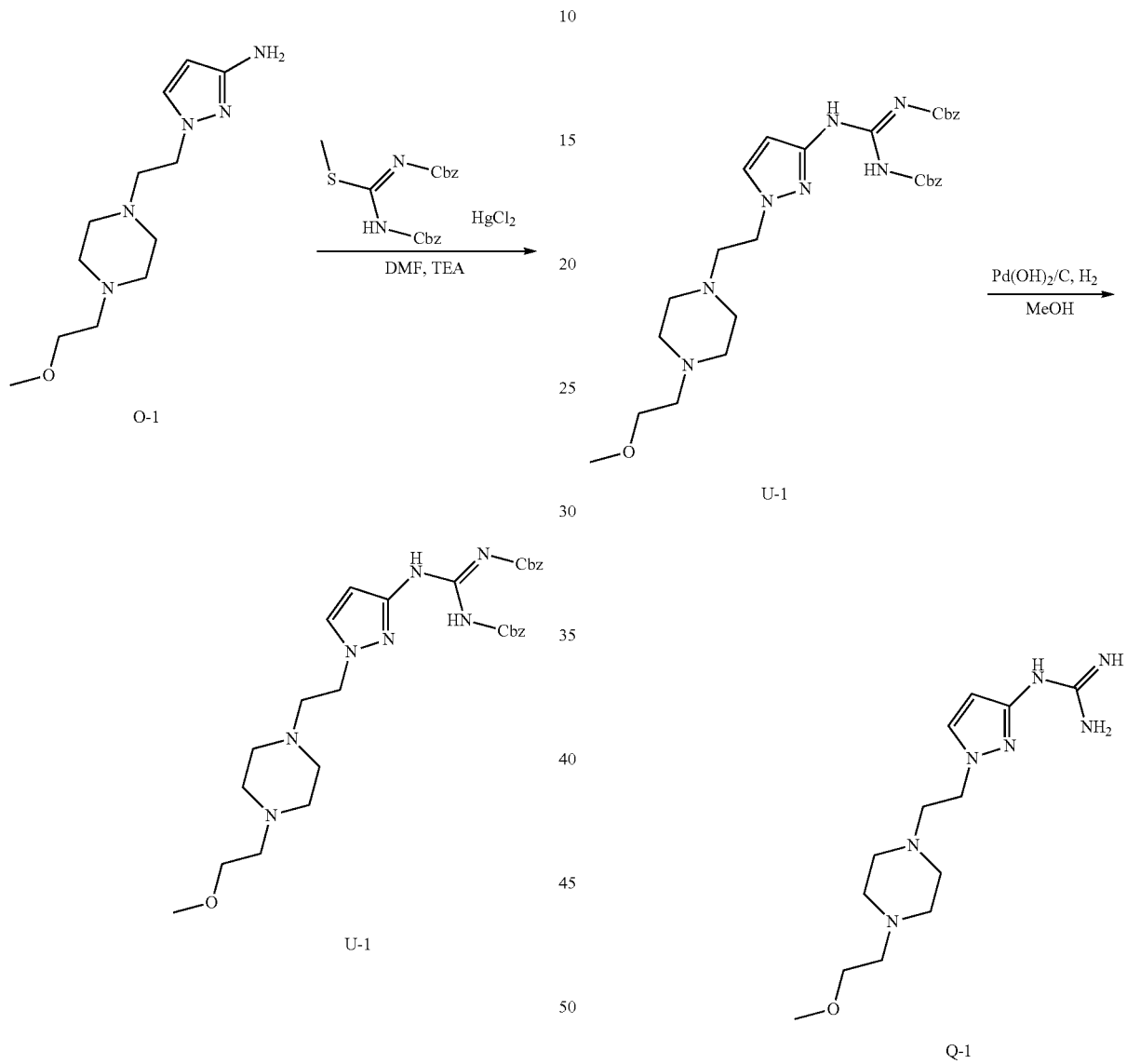

residue is purified by column chromatography with heptane/EtOAc (80:20-20:80 gradient) followed by DCM/MeOH (100:0-95:5 gradient) as the eluent to give the title compound U-1 (3.57 g, 81%) as a yellow oil ($t_{Ret}$=1.79 min, $[M+H]^+$=564, HPLC method A).

Synthesis of N-(1-{2-[4-(2-methoxy-ethyl)-piperazin-1-yl]-ethyl}-1H-pyrazol-3-yl)-guanidine Q-1

HgCl$_2$ (2.36 g, 8.6 mmol) is added to a stirred solution of 1,3-bis(benzyloxycarbonyl)-2-methyl-2-thiopseudourea (3.0 g, 8.21 mmol), 1-{2-[4-(2-methoxy-ethyl)-piperazin-1-yl]-ethyl}-1H-pyrazol-3-ylamine O-1 (2.0 g, 7.82 mmol) and TEA (2.42 mL, 17.19 mmol) in anhydrous DMF (5 mL) at 0° C. and the mixture is stirred at 0° C. for 2 h and at rt overnight. The mixture is filtered through Celite®, washed with EtOAc (50 mL) and the filtrate is concentrated in vacuo. The residue is redissolved in EtOAc (90 mL) and washed with water (2×10 mL). The organic phase is dried (Na$_2$SO$_4$), filtered and concentrated in vacuo. The crude Pd(OH)$_2$ on charcoal (10%; 300 mg) is added to a solution of intermediate U-1 (3.57 g, 6.33 mmol) in MeOH (20 mL) and the mixture is stirred under an atmosphere of hydrogen at rt for 48 h. The mixture is filtered through Celite®, washed with MeOH and concentrated in vacuo to give the title compound Q-1 (1.7 g, 91%) as a pale yellow oil.

Q-2 can be prepared analogously in this two step sequence.

TABLE 5

| # | structure | t_ret [min] | [M + H]+ | HPLC method |
|---|---|---|---|---|
| P | (pyrazole with guanidino group and N-2-hydroxyethyl substituent) | 0.26 | 170 | A |
| Q-1 | (pyrazole with guanidino group and N-ethyl-[4-(2-methoxyethyl)piperazin-1-yl] substituent) | 0.28 | 296 | A |
| Q-2 | (pyrazole with guanidino group and N-(2-morpholinoethyl) substituent) | 0.25 | 239 | A |
| Q-3 | (pyrazole with guanidino group and N-[2-(4-methylpiperazin-1-yl)ethyl] substituent) | n.a. | n.a. | |

43

Synthesis of 2-[3-((R)-5,8-dimethyl-9-phenyl-5,8-dihydro-6H-pyrazolo[3,4-h]quinazolin-2-ylamino)-pyrazol-1-yl]-ethanol (Intermediate R)

44

Synthesis of Methanesulfonic Acid 2-[3-((R)-5,8-dimethyl-9-phenyl-5,8-dihydro-6H-pyrazolo[3,4-h]quinazolin-2-ylamino)-pyrazol-1-yl]-ethyl Ester (Intermediate S)

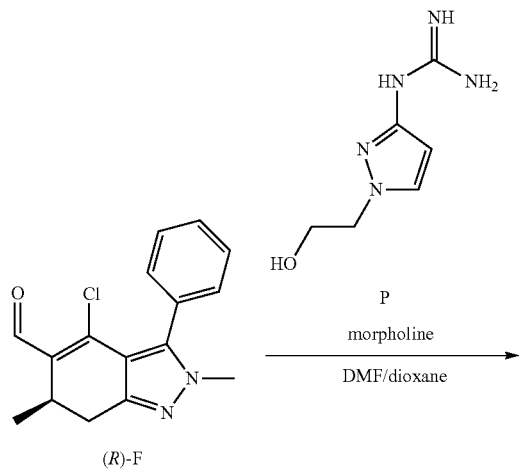

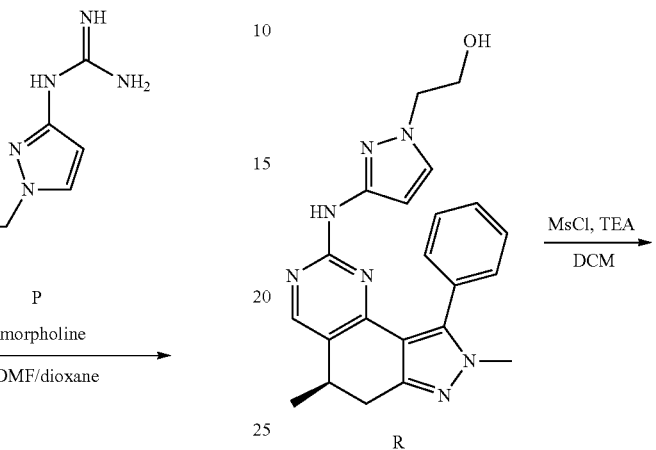

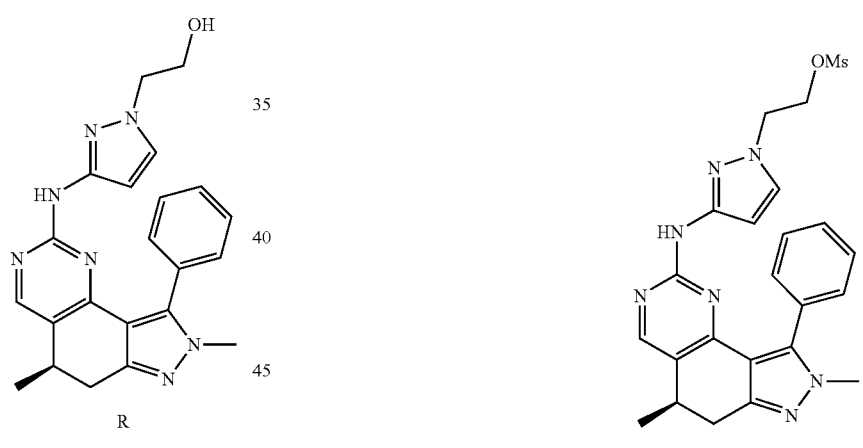

Intermediate (R)-F (3.58 g, 12.5 mmol, 1 eq.) is dissolved in dioxane (10 mL) and guanidine P (2.12 g, 12.5 mmol, 1 eq.) is added. After addition of morpholine (7.1 mL, 81.3 mmol, 6.5 eq.) the reaction mixture is heated to 120° C. in a microwave and stirred 45 min at this reaction temperature. The reaction mixture is poured into water and extracted with DCM. The organic layer is dried over magnesium sulfate and evaporated in vacuo. Purification with normal phase chromatography on silica with MeOH/DCM yields 1.7 g (4.23 mmol, 34%) of intermediate R ($t_{ret}$ [min]=1.22, [M+H]$^+$=362, HPLC method C).

Intermediate R (900 mg, 2.42 mmol, 1 eq.) is suspended in DCM (2 mL) and subsequently TEA (0.45 g, 4.48 mmol, 2 eq.) and methanesulfonyl chloride (0.32 g, 2.0 mmol, 1.3 eq.) are added. The reaction mixture is stirred for 40 min at rt and is poured into saturated aqueous sodium bicarbonate solution afterwards. Extraction with DCM, drying over magnesium sulfate and evaporation in vacuo gives 1.2 g of the crude mesylate S ($t_{ret}$ [min]=1.56, [M+H]$^+$=480, HPLC method D).

Synthesis of 4-{2-[3-((R)-5,8-dimethyl-9-phenyl-5,8-dihydro-6H-pyrazolo[3,4-h]quinazolin-2-ylamino)-pyrazol-1-yl]-ethyl}-piperazine-1-carboxylic Acid tert-butyl Ester (Intermediate T)

Synthesis of Compounds (I) According to the Invention

Synthesis of Compound I-1

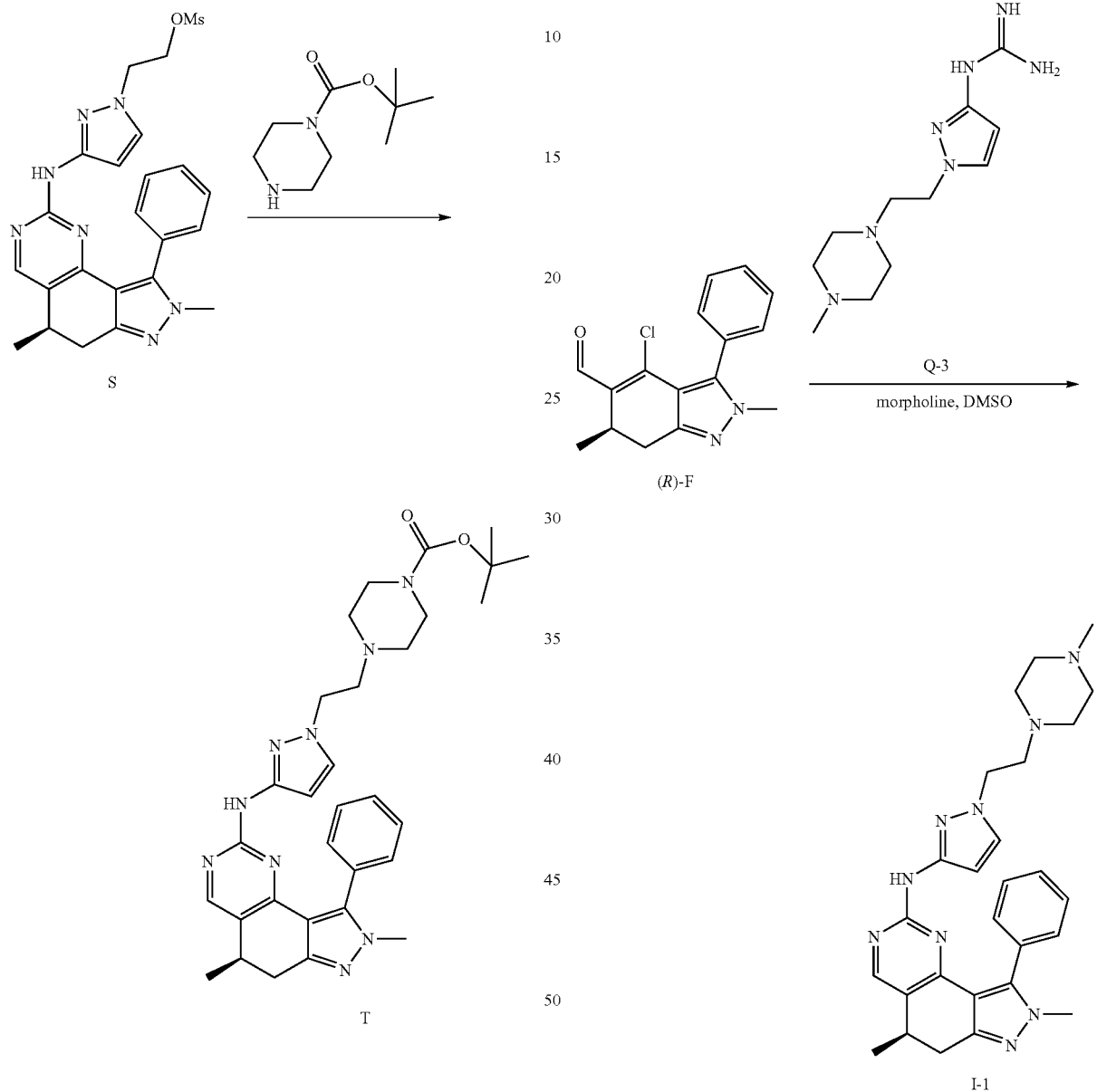

The crude mesylate S obtained (102 mg, 0.2 mmol, 1 eq.) is dissolved in DMF (2 mL). Piperazine-1-carboxylic acid tert-butyl ester (59 mg, 0.3 mmol, 1.5 eq) and DIPEA (55 mg, 0.4 mmol, 2 eq.) is added. The reaction mixture is stirred 4 h at 80° C. and is then directly chromatographed by normal phase chromatography on silica with MeOH/DCM to yield 66 mg (0.12 mmol, 69%) of T ($t_{ret}$ [min]=1.31, [M+H]$^+$=570, HPLC method C).

Intermediate (R)-F (125 mg, 0.44 mmol, 1 eq.) is dissolved in DMSO (0.75 mL) and morpholine (192 mg, 2.20 mmol, 5 eq.) is added. After addition of guanidine Q-3 (143 mg, 0.60 mmol, 1.4 eq.) the reaction mixture is heated to 135° C. in a microwave and stirred 30 min at this reaction temperature. The product is precipitated by addition of water/EtOH (500 µL; 1:1) at rt. The precipitate is washed with water and EtOH and dried to yield 105 mg (0.22 mmol, 51%) of I-1.

Compound I-2 can be obtained in an analogous manner with guanidine Q-2.

Synthesis of Compound I-3

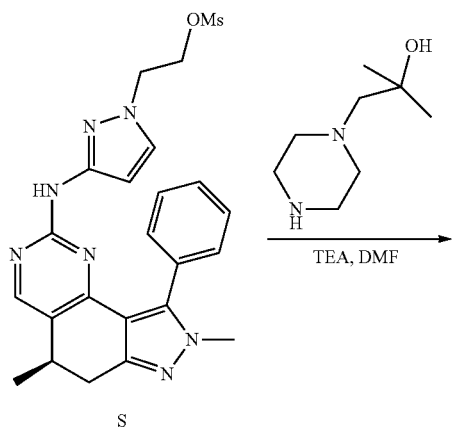

Synthesis of Compound I-12

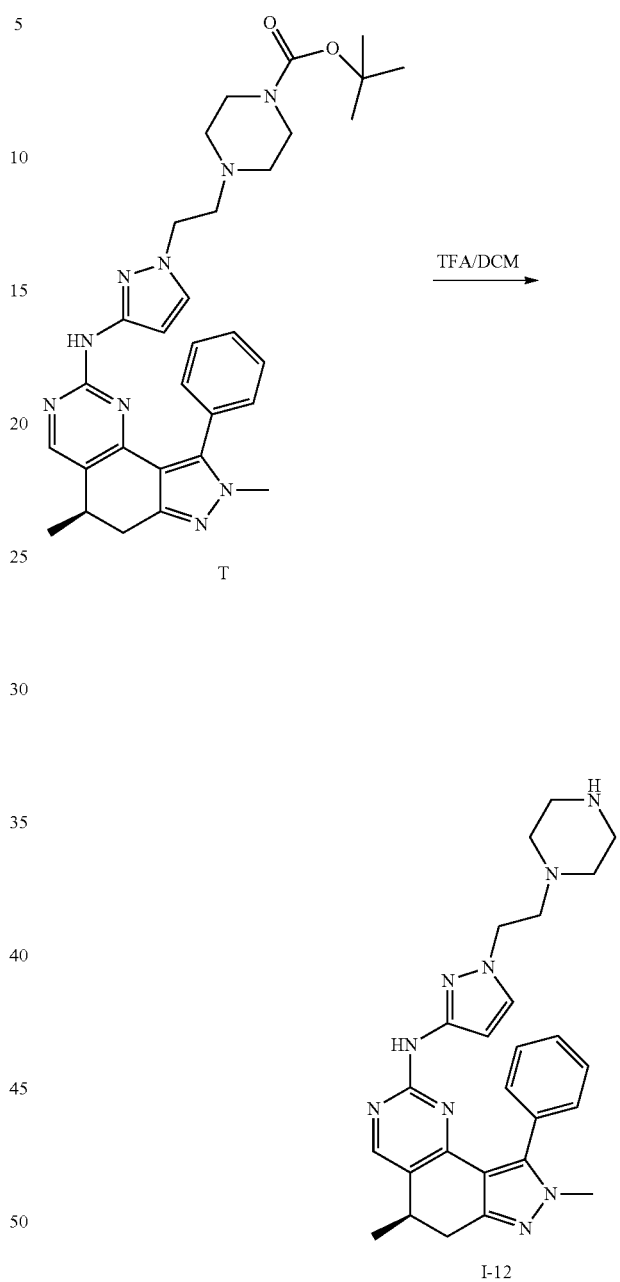

The crude mesylate S obtained (1.2 g) is dissolved in DMF (2 mL). 2-methyl-1-piperazin-1-yl-propan-2-ol (700 mg, 3.75 mmol, 1.5 eq) and DIPEA (647 mg, 5 mmol, 2 eq.) is added. The reaction mixture is stirred overnight at 80° C. and is then directly chromatographed by normal phase chromatography on silica with MeOH/DCM to yield 898 mg (1.58 mmol, 63%) of I-3.

Compounds I-5, I-7, I-9, I-10 and I-11 can be obtained in an analogous manner starting with intermediate S and the respective piperazine or piperazionone derivative (commercially available) as nucleophile.

Intermediate T (898 mg, 1.58 mmol, 1 eq.) is dissolved in DCM (10 mL) and TFA (3.59 g, 31.5 mmol, 20 eq.) is added. The mixture is stirred overnight and poured into water. The pH is adjusted slightly basic by addition of 1 M NaOH. Extraction with DCM, drying of the organic phase over magnesium sulfate and subsequent evaporation in vacuo yields 750 mg (1.58 mmol, quant.) of the crude I-12.

Synthesis of Compound I-6

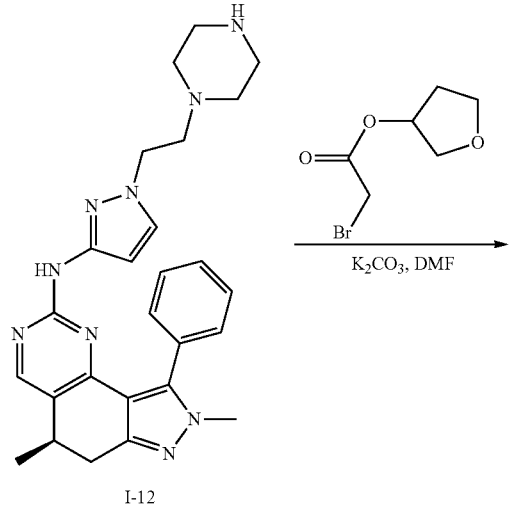

I-12

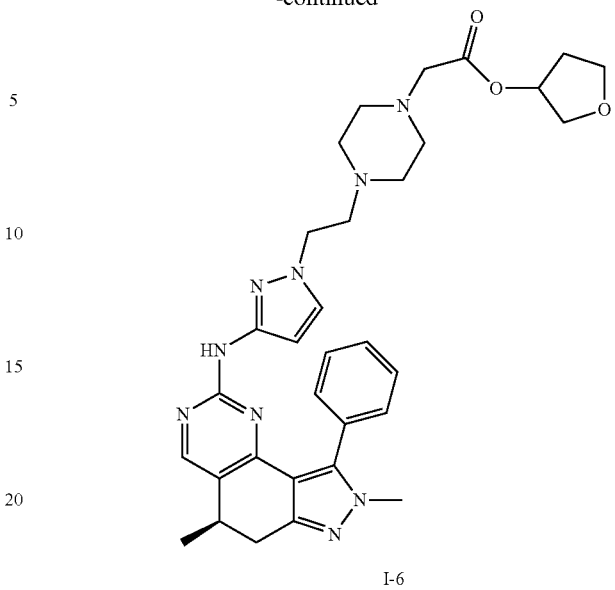

I-6

Compound I-12 (120 mg, 0.26 mmol, 1 eq.) is dissolved in DMF (0.5 mL) and potassium carbonate (106 mg, 0.77 mmol, 3 eq.) is added. After addition of bromo-acetic acid tetrahydro-furan-3-yl ester (108 mg, 0.52 mmol, 2 eq.) the reaction is stirred for 4 h at rt. The mixture is filtered and RP chromatography (basic buffer) yields 72 mg (0.12 mmol, 47%) of I-6. (Bromo-acetic acid tetrahydro-furan-3-yl ester is readily available by reacting bromoacetylchloride with 3-hydroxytetrahydrofuran in DCM at 0° C. for 1 h.)

Compounds I-4 and I-8 can be obtained in an analogous manner starting with I-12 and the respective α-bromo acid esters.

TABLE 6

| # | structure | $t_{ret.}$ [min] | $[M + H]^+$ | HPLC method |
|---|---|---|---|---|
| I-1 | Chiral | 1.05 | 484 | C |

TABLE 6-continued
| # | structure | $t_{ret.}$ [min] | [M + H]$^+$ | HPLC method |
|---|---|---|---|---|
| I-2 | 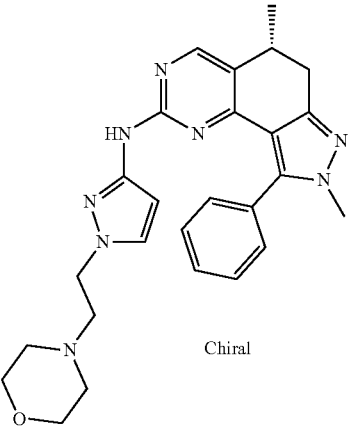 [SMILES: C[C@@H]1Cc2nn(C)c(-c3ccccc3)c2-c2nc(Nc3ccn(CCN4CCOCC4)n3)ncc21] Chiral | 1.06 | 471 | C |
| I-3 | 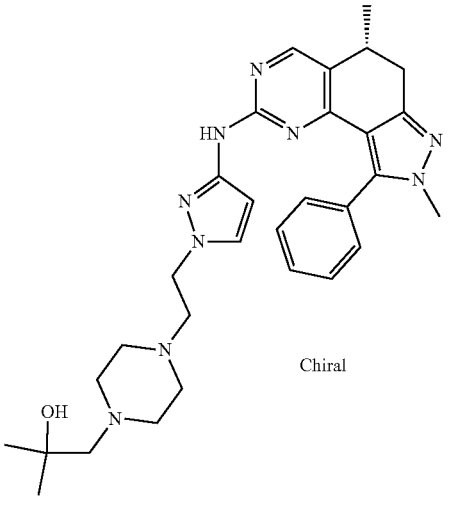 [SMILES: C[C@@H]1Cc2nn(C)c(-c3ccccc3)c2-c2nc(Nc3ccn(CCN4CCN(CC(C)(C)O)CC4)n3)ncc21] Chiral | 1.12 | 542 | C |
| I-4 | 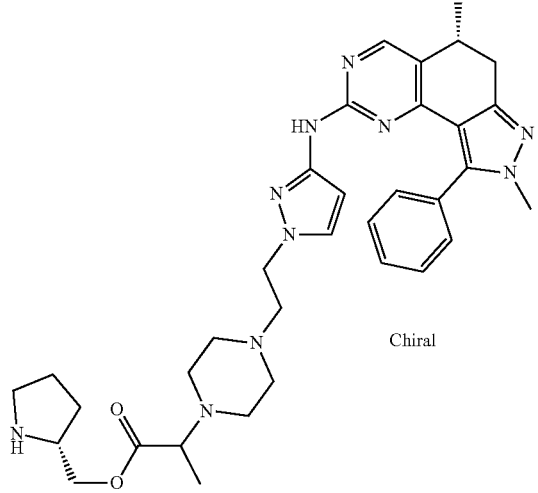 [SMILES: CC(C(=O)OC[C@H]1CCCN1)N1CCN(CCn2ccc(Nc3ncc4c(n3)-c3c(nn(C)c3-c3ccccc3)C[C@H]4C)n2)CC1] Chiral | 1.01 | 625 | C |

TABLE 6-continued
| # | structure | $t_{ret.}$ [min] | [M + H]⁺ | HPLC method |
|---|---|---|---|---|
| I-5 | 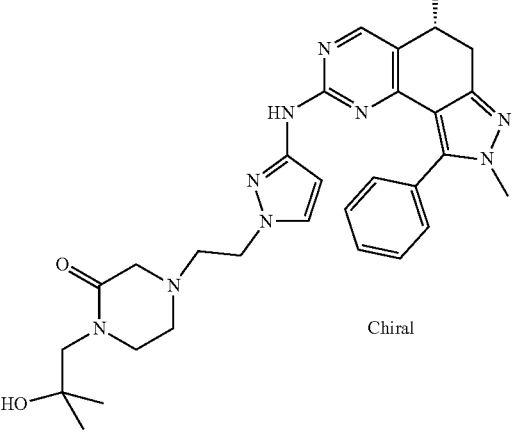 Chiral | 1.01 | 556 | C |
| I-6 | 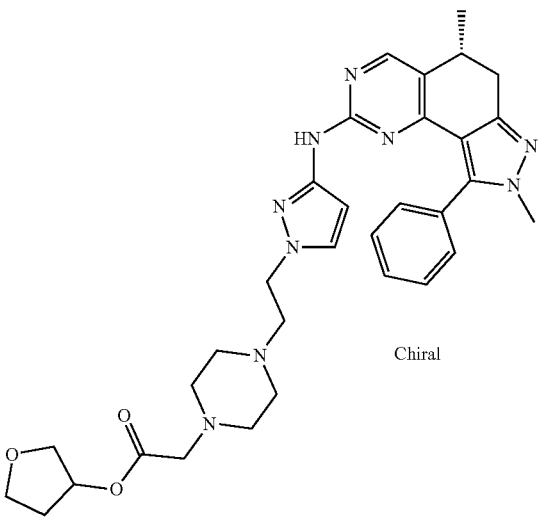 [SMILES: C[C@@H]1Cc2nn(C)c(-c3ccccc3)c2-c2nc(Nc3ccn(CCN4CCN(CC(=O)OC5CCOC5)CC4)n3)ncc21] Chiral | 1.08 | 598 | C |
| I-7 | 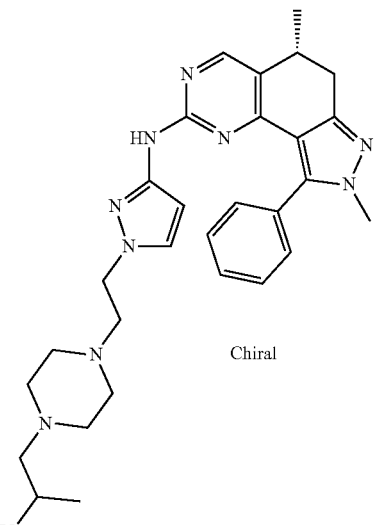 Chiral | 1.04 | 528 | C |

TABLE 6-continued
| # | structure | $t_{ret.}$ [min] | $[M + H]^+$ | HPLC method |
|---|---|---|---|---|
| I-8 | 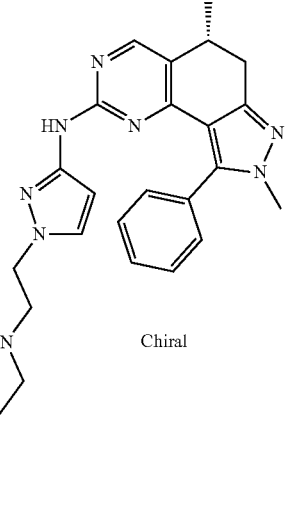 Chiral | 1.11 | 612 | C |
| I-9 | 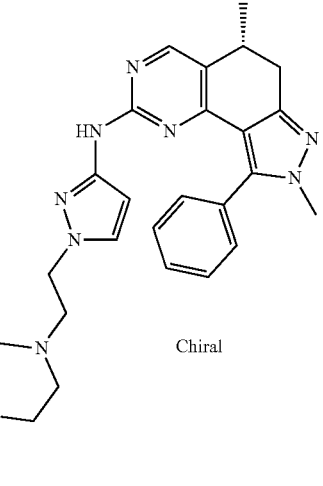 Chiral | 1.13 | 554 | C |
| I-10 | 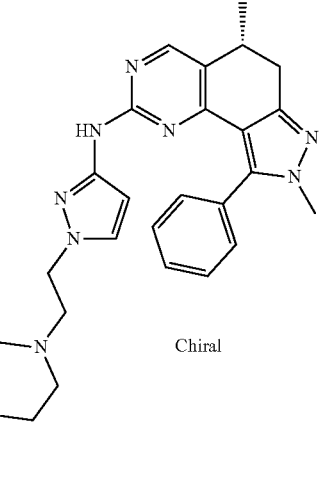 Chiral | 0.98 | 514 | C |

TABLE 6-continued

| # | structure | $t_{ret.}$ [min] | $[M + H]^+$ | HPLC method |
|---|---|---|---|---|
| I-11 | 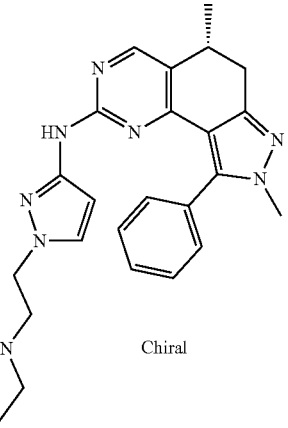 Chiral | 1.09 | 528 | C |
| I-12 | 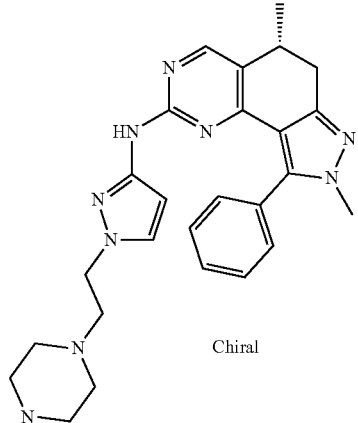 Chiral | 0.74 | 470 | F |

The following Examples describe the biological activity of the compounds according to the invention, without restricting the invention to these Examples:

Hyperglycemia is an inherent tolerability risk associated with inhibition of IGF-1R/IR. This is likely due to the important role of the IGF-1R/IR in glucose disposal. The inventors were surprised to find that specific pharmacokinetic (PK) properties of the IGF-1R/IR inhibitors, for example in vivo half-life, influenced the duration of hyperglycemia induction in rodents. Rapid in vivo elimination of the IGF-1R/IR inhibitors was associated with concomitant normalization of blood glucose levels. As such it was believed that this short duration of hyperglycemia would be beneficial regarding tolerability of IGF-1R/IR inhibitors.

Surprisingly, the inventors found that compounds (I) according to the invention substantially possess these desirable PK properties. In particular, it turned out that the fine-tuning of PK properties could be readily accomplished by variation of the substituent group located in the 2-position of the 5,8-dihydro-6H-pyrazolo[3,4-h]quinazoline scaffold. A substituted 1H-pyrazol-3-yl-amino group as defined herein proved to be especially suitable. In particular, a proper decoration with a solubilizing group attached to the 1H-pyrazol-3-yl-amino moiety via an ethyl spacer proved to be beneficial. The basicity and lipophilicity of this terminal solubilizing group was shown to have a pronounced effect on the overall DMPK properties. Here especially the choice of moderately basic and liphophilic 6-membered heteroaliphatic moieties result in desirable PK properties of the final compounds (I).

Prior art document WO 2012/010704, which is completely silent about the pharmacokinetic profile of its compounds, discloses compounds with similar substituents in the 2-position, e.g. compounds I-166, I-167 and I-175, which share the previously undefined, desirable pharmacokinetic profile with compounds (I) according to the invention. However, these compounds suffer from the drawback that they are not very selective, i.e. they significantly inhibit kinases other than IGF-1R/IR as shown in a kinase selectivity panel of 32 diverse kinases (standard panel of 30 kinases+MAPK8 and MAPK9) representatively selected from the human kinome (see table 8).

Pharmacological inhibition of the IGF-1R is associated with specific tolerability concerns in some humans. For example, antibody inhibitors of the IGF-1R including figitumumab (Haluska et al, 2007; Haluska et al, 2010) and ganitumab (Tolcher et al, 2009) are associated with toxicities in some humans including but not limited to hyperglycemia, thrombocytopenia, fever, rash, nausea, anorexia, diarrhea, hyperuracemia and fatigue. As such, it was a second aim to develop small molecule compounds which are highly specific inhibitors of the IGF-1R kinase function and sparing of off-target kinases associated with tolerability liabilities. In doing so, the tolerability risks of these compounds would be limited to those associated with IGF-1R inhibition alone.

Surprisingly, higher selectivity (and higher cellular potency) could be obtained by the introduction of a chiral methyl group in the central ring of the 5,8-dihydro-6H-pyrazolo[3,4-h]quinazoline scaffold.

Structurally related compounds disclosed in WO 2012/010704, e.g. compounds I-166, I-167 and I-175, demonstrate relatively high cellular potency on HCT 116 colorectal cancer cells, a cell line whose proliferation is known to be independent from IGF-1R signaling (see below). Thus, the inhibitor activity on HCT 116 cells must be due to undesired off-target effects of an unselective inhibitor compound.

In particular, compounds I-166 and/or I-167 demonstrate elevated inhibition (>50% inhibition at 1 µM) of the kinases FGFR1, MAPK8 (JNK1), MAPK9 (JNK2), MAP2K1 (MEK1), STK6 (Aurora A), PAK4 and RAF1. Pharmacological inhibition or genetic deletion of these kinases is associated with specific risks or tolerability concerns as outlined below. Compounds (I) according to the invention show reduced inhibition of these kinases. As such this demonstrates an improvement in the profile of these new compounds with regards to potential tolerability and safety risks.

The small molecule kinase inhibitors of the FGFR family of proteins (FGFR1/2/3) such as Dovitinib (TK1258) (Andre et al, 2013; Angevin et al, 2013) and Nintedanib (BIBF 1120) (Droz et al, 2014; Richeldi et al, 2014) display tolerability concerns in some humans including but not limited to gastrointestinal, skin and subcutaneous tissue disorders, asthenia and abnormalities in liver function tests and diarrhea. It was considered important for compounds according to the invention to be selective against the FGFR family of proteins.

Knock-out of the kinase MAPK8 (JNK1) in mice leads to the spontaneous development of tumors in the intestine (Tong et al, 2007). A second study indicated that MAPK8 knockout mice demonstrate an increased incidence of skin tumor development upon 12-O-tetradecanoylphorbol-13-acetate (TPA)-treatment compared to wild-type littermates (She et al, 2002). Knockout of the closely related protein MAPK9 (JNK2) led to an earlier incidence of mammary tumor development in Polyoma Middle T Antigen transgene expressing mice (Chen et al, 2010). Together, these data raise the possibility that MAPK8 and MAPK9 exert tumor suppressor functions and that interference with their activity could potentially result in a risk of tumorigenesis. As such it was considered important that the compounds generated in this application demonstrate selectivity against MAPK8 and MAPK9.

Pharmacological inhibition of the protein MAP2K1 (MEK1) with the compounds Trametinib (GSK1120212) or Selumetinib (AZD6244) has led to tolerability concerns in some humans including but not limited to dermatological and gastrointestinal toxicity and fatigue (Farley et al, 2013; Kim et al, 2013). It was considered important for the compounds generated in this application be selective against MAP2K1.

Experimental data have shown that conditional knock-out of the kinase PAK4 in the secondary heart field led to a range of cardiac abnormalities (Nekrasova et al, 2012). This data raises the possibility that inhibition of PAK4 could potentially be associated with cardiac toxicity. It was considered important that the compounds generated in this application demonstrate selectivity against PAK4.

Pharmacological inhibition of the RAF family of kinases (A-Raf, B-Raf, C-Raf [Raf-1]) with the compounds Vemurafenib (PLX4032) (McArthur et al, 2014) or Dabrafenib (GSK2118436) (Ascierto et al, 2013; Falchook et al, 2012) have led to tolerability concerns in some humans including but not limited to arthralgia, pyrexia, fatigue, headache, alopecia, keratoacanthoma, nausea, rash and the development of cutaneous squamous-cell carcinomas. It was considered important for the compounds generated in this application be selective against the RAF family.

Pharmacological inhibition of the Aurora family of kinases (Aurora A [STK6], Aurora B, Aurora C) with the compounds Barasertib (AZD1152) (Kantarjian et al, 2013), Alisertib (MLN8237) (Falchook et al, 2014) or AT9283 (Foran et al, 2014) have led to tolerability concerns in some humans including but not limited to stomatitis and febrile neutropenia. It was considered important for the compounds generated in this application be selective against the Aurora family.

Overall, compounds (I) according to the invention generally show an improved selectivity profile in relation to the structurally closest compounds in WO 2012/010704 (see table 8), i.e. less kinases are significantly inhibited (% inhibition>50% at 1 µM) and/or the % inhibition of individual kinases is very often lower for compounds (I).

Insulin-Like Growth Factor-1 Receptor (IGF-1R)-Kinase Assay

The kinase activity is measured by DELFIA® assay (dissociation-enhanced lanthanide fluorescence immunoassay, Perkin Elmer). The cytoplasmic kinase domain of human IGF-1R (amino acids 964-1370) is expressed as a fusion protein with a glutathione-S-transferase tag (IGF-1R-GST) in High Five™ Cells (Invitrogen). Enzyme activity is measured in the presence of substances and a control substance. Poly-glutamate-tyrosine peptide (pEY, Sigma Aldrich) and biotinylated pEY (bio-pEY) are used as reaction substrates.

10 µL of substance in 25% DMSO are mixed with 30 µL of IGF-1R-GST solution (67 mM HEPES pH 7.4, 15 µg/mL pEY, 1.7 µg/mL bio-pEY, 13.3 mM $MgCl_2$, 3.3 mM dithiothreitol, 0.0033% Brij 35, 2 ng IGF-1R-GST) in 96-well plates. The reactions are started with 10 µL of a 750 µM ATP solution. After 40 min at RT the reactions are stopped with 50 µL of stop solution (250 mM EDTA, 20 mM HEPES pH 7.4). 90 µL from each reaction are transferred onto streptavidin-coated 96-well plates. After 120 min incubation at RT the plates are washed three times with 200 µL phosphate-buffered saline (PBS) per well. The plates are incubated for 60 min with 100 µL of europium-coupled antibody against phospho-tyrosine (diluted 1/2000 in Perkin Elmer DELFIA assay buffer) per well. The plates are washed three times with 200 µL per well of DELFIA washing buffer (Perkin Elmer). 100 µL DELFIA Enhancement Solution (Perkin Elmer) is added to each well, and the plates are incubated for 10 min. The fluorescence signal is measured with a Wallac Victor TRF Reader. $IC_{50}$ values for the inhibition of the IGF-1R-kinase activity are calculated using the programme GraphPad (Version 3.0).

Table 7 shows the $IC_{50}$ values of example compounds and prior art compounds determined using the above assay.

Cellular IGF-IR-phosphorylation Assay

The activity of substances against the phosphorylation of IGF-1R in activated cells is to measured as follows: mouse fibroblast cells (transfected with human IGF-1R, FibrohIGF-1R) are cultivated in standard medium (DMEM, 10% foetal calf serum (FCS, Gibco), 1×MEM Non-Essential Amino Acids (NEAA, Gibco), 7.5% sodium hydrogen carbonate (Gibco) and 0.3 mg/mL Puromycin (Sigma)) in a humid incubator at 37° C. with 5% $CO_2$/95% air.

10000 Fibro-hIGF-1R cells per well in 200 µL of standard medium are seeded into 96-well plates and cultivated overnight. The next day, the medium is suction filtered and the cells are cultivated in 90 µL serum-reduced medium (DMEM, 0.5% FCS, 1×MEM NEAA, 7.5% sodium hydrogen carbonate) for a further 24 h. 10 µL of substance solution (diluted in serum-reduced medium) is added thereto, and the cells are incubated for a further 120 min in the incubator. The phosphorylation of IGF-1R is activated for 30 min by the addition of IGF-1 (20 ng/mL in serum-reduced medium). All further incubations are carried out at RT. The supernatant is suction filtered from the wells, and the cells are fixed in 100 µL per well of 4% paraformaldehyde (diluted in PBS). The supernatant in the well is suction filtered and the cells are permeabilised for 5 min in 300 µL per well of 0.1% TritonX-100 (diluted in PBS). The supernatants are suction filtered once again and the cells are incubated for 20 min in quenching buffer (PBS with 0.1% TritonX-100 and 1.2% hydrogen peroxide), to inhibit the endogenous peroxidase of the cells. The cells are washed for 5 min with 300 µL per well of PBS with 0.1% TritonX-100 and then incubated for 60 min with 100 µL per well of blocking buffer (PBS with 0.1% TritonX-100 and 5% Bovine Serum Albumin (BSA)). The blocking buffer is exchanged for 50 µL of the first antibody buffer (1/1000 dilute anti-phospho-IGF-1 receptor β (Tyr1135/1136)/insulin receptor β (Tyr1150/1151) (19H7) rabbit monoclonal antibody from Cell Signaling Technology in blocking buffer) and the plates are incubated overnight at 4° C. The next day the plates are washed for 5 min with 300 µL PBS/0.1% TritonX-100 at RT and then incubated for 60 min with 50 µL per well of the second antibody buffer (1/500 diluted Goat Anti-Rabbit Immunoglobulin-Horseradish Peroxidase (HRP) (Dako) in blocking buffer) at RT. The plates are washed first for 5 min with 300 µL PBS/0.1% TritonX-100 and then for a further 5 min with 300 µL PBS at RT. The plates are developed for 10 min with 100 µL per well of a peroxidase solution (1:1 mixture of TMB Peroxidase Substrate and Peroxidase Solution B from Kirkegaard & Perry Laboratories, Inc.). The reactions are stopped with 100 µL per well of stop solution (1M phosphoric acid). The absorbance in each well is measured at 450 nm with a SpectraMax Absorbance Reader. $EC_{50}$ values for inhibiting the phosphorylation of the IGF-1R in activated cells are calculated using the programmes Fifty (Version 2) and GraphPad (Version 3.0).

Cell Proliferation Assays

Compounds were tested for their anti-proliferative effects in the TC-71 (Ewing's sarcoma) and HCT 116 (colorectal carcinoma) cancer cell lines in vitro. Published scientific data has described that interference with the IGF-1R signaling pathway reduces the proliferation of TC-71 cells (Manara et al, 2007). Therefore TC-71 cells served as a positive control cell line for monitoring the activity of compounds against IGF-1R-mediated cell proliferation. In contrast, published data has demonstrated that the proliferation of HCT 116 cells is independent of IGF-1R signaling (Pitts et al, 2010). Therefore the HCT 116 cell line served as a negative control.

2000 TC-71 cells or 1000 HCT 116 cells were seeded per well in 180 µL IMDM+10% foetal calf serum (FCS)+ penicillin/streptomycin into 96-well microtitre plates. The plates were placed in a cell culture incubator (37° C. in a humidified atmosphere of 95% $O_2$/5% $CO_2$) overnight. The following day, serial dilutions of compounds, prepared in duplicates, were transferred onto the cell layers (controls without compound). The cells were cultivated for a further 72 h in the cell culture incubator. 20 µL of Alamar Blue™ (Serotec Ltd, Dusseldorf, Germany) was added to each well and the plates incubated for 7 h in the cell culture incubator. Fluorescence (extinction wavelength of 544 nm and emission at 590 nm) was then measured and the normalized data fitted by iterative calculation with a sigmoidal curve analysis program (Graph Pad Prism) with a variable Hill slope to determine the $EC_{50}$ values.

Table 7 shows the $EC_{50}$ values of example compounds and prior art compounds determined using the above assays (TC-71 and HCT 116).

TABLE 7

| # | IGF-1R [nM] | TC71 [nM] | HCT 116 [nM] |
|---|---|---|---|
| I-1 | 0.9 | 2.62 | >2500 |
| I-2 | 1.3 | 2.35 | >2500 |
| I-3 | 1.9 | 2.67 | 2000 |
| I-4 | 1.5 | 6.82 | >2500 |
| I-5 | 4.8 | 4 | >2500 |
| I-6 | 1.1 | 5 | >2500 |
| I-7 | 1.0 | 2.17 | 1835 |
| I-8 | 2.8 | 5.98 | >2500 |
| I-9 | 1.2 | 5.43 | >2500 |
| I-10 | 2.2 | 5.93 | >2500 |
| I-11 | 0.9 | 3.74 | >2500 |
| I-166 in WO 2012/010704 | 0.6 | 9.77 | 632.3 |
| I-167 in WO 2012/010704 | 0.6 | 5.28 | 511.7 |
| I-175 in WO 2012/010704 | 0.4 | 3.64 | 296.59 |

In addition to TC-71, several other cancer cell lines from diverse tissue origins were shown to be sensitive to IGF-1R/IR inhibition including ABC-1 (non-samll cell lung cancer), LS1034 (colon cancer), NCI-H295R (adrenal gland carcinoma), BE(2)-C (neuroblastoma), HEP 3B2.1-7 (liver carcinoma) and RH-41 (rhabdomyosarcoma).

REFERENCE LIST

F. Andre et al., Clin. Cancer Res. 19 (2013) 3693-3702.
E. Angevin et al., Clin. Cancer Res. 19 (2013) 1257-1268.
P. A. Ascierto et al., J Clin. Oncol. 31 (2013) 3205-3211.
P. Chen et al., PLoS One. 5 (2010) e10443.
J. P. Droz et al., Anticancer. Drugs (2014).
G. Falchook et al., Invest. New. Drugs (2014).
G. S. Falchook et al., Lancet. 379 (2012) 1893-1901.
J. Farley et al., Lancet. Oncol. 14 (2013) 134-140.
J. Foran et al., Clin. Lymphoma. Myeloma. Leuk. 14 (2014) 223-230.
P. Haluska et al., Clin. Cancer Res. 13 (2007) 5834-5840.
P. Haluska et al., Cancer Chemother. Pharmacol. 65 (2010) 765-773.
H. M. Kantarjian et al., Cancer 119 (2013) 2611-2619.
K. B. Kim et al., J Clin. Oncol. 31 (2013) 482-489.
M. C. Manara et al., Clin. Cancer Res. 13 (2007) 1322-1330.
G. A. McArthur et al., Lancet. Oncol. 15 (2014) 323-332.
T. Nekrasova et al., Transgenic. Res. 21 (2012) 797-811.
T. M. Pitts et al., Clin Cancer Res. 16 (2010) 3193-3204.
L. Richeldi et al., N. Engl. J Med 370 (2014) 2071-2082.
Q. B. She et al., Cancer Res. 62 (2002) 1343-1348.
A. W. Tolcher et al., J Clin. Oncol. 27 (2009) 5800-5807.

C. Tong et al., Am. J Pathol. 171 (2007) 297-303.

Kinase Selectivity Assays

In order to compare the kinase selectivity of compounds (I) according to the invention with known prior art compounds the commercially provided SelectScreen® Kinase Profiling Service (Z'-LYTE®) was used (Life Technologies GmbH, Darmstadt, Germany) to investigate the ability of the compounds to inhibit a number of different, representatively selected human kinases. Further details regarding this service are available on the Life Technologies website at http://www.lifetechnologies.com/de/en/home/products-and-services/services/custom-services/screening-and-profiling-eces/seectsceenpling-service/selectscreen-kinase-profiling-service.html and are also provided below ("Z'-LYTE® Screening Protocol and Assay Conditions").

All kinases are also commercially available together with respective Z'-LYTE® Kinase Assay Kits in convenient platform-ready assay formats from Life Technologies (see order numbers below) or other suppliers and assays can be performed according to the procedures recommended by the manufacturer.

Assay Theory:

The Z'-LYTE® biochemical assay employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair.

In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress, as shown in the equation below.

$$\text{Emission Ratio} = \frac{\text{Coumarin Emission (445 nm)}}{\text{Fluorescein Emission (520 nm)}}$$

A significant benefit of this ratiometric method for quantitating reaction progress is the elimination of well-to-well variations in FRET-peptide concentration and signal intensities. As a result, the assay yields very high Z'-factor values (>0.7) at a low percent phosphorylation.

Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

Z'-LYTE® Assay Conditions:
Test Compounds
   The Test Compounds are screened at 1 µM.
Peptide/Kinase Mixtures
   All Peptide/Kinase Mixtures are diluted to a 2× working concentration in the appropriate Kinase Buffer (see Kinase Specific Assay Conditions below for a complete description).
ATP Solution
   All ATP Solutions are diluted to a 4× working concentration in Kinase Buffer (50 mM HEPES pH 7.5, 0.01% BRIJ-35, 10 mM $MgCl_2$, 1 mM EGTA).
   ATP Km apparent is previously determined using a Z'-LYTE® assay.
Development Reagent Solution
   The Development Reagent is diluted in Development Buffer (see Kinase-Specific Assay Conditions below for a complete description).
10× Novel PKC Lipid Mix:
   2 mg/mL Phosphatidyl Serine, 0.2 mg/mL DAG in 20 mM HEPES, pH 7.4, 0.3% CHAPS
   For 5 mL 10× Novel PKC Lipid Mix:
1. Add 10 mgs Phosphatidyl Serine (Avanti Polar Lipids Part#8400032C or 840039C) and
1 mg DAG (Avanti Polar Lipids Part#800811C) to a glass tube.
2. Remove the chloroform from lipid mixture by evaporating to a clear, thin film under a stream of nitrogen. Continuous rotation of the tube, at an angle to ensure maximum surface area of the lipid solution, will promote the thinnest film.
3. Add 5 mLs resuspension buffer, 20 mM HEPES, 0.3% CHAPS, pH 7.4, to the dried lipid mix
4. Heat gently to 50-60° C. for 1-2 minutes and vortex in short intervals until the lipids are dissolved to a clear or slightly hazy solution. The lipids are typically in solution after 2-3 heat/vortex cycles.
5. Cool to room temperature, aliquot into single use volumes and store at −20° C.
Assay Protocol
Bar-Coded Corning, Low Volume NBS, Black 384-Well Plate (Corning Cat. #4514)
1. 2.5 µL—4× Test Compound or 100 nL 100× plus 2.4 µL kinase buffer
2. 5 µL—2× Peptide/Kinase Mixture
3. 2.5 µL—4×ATP Solution
4. 30-second plate shake
5. 60-minute Kinase Reaction incubation at room temperature
6. 5 µL—Development Reagent Solution
7. 30-second plate shake
8. 60-minute Development Reaction incubation at room temperature
9. Read on fluorescence plate reader and analyze the data
Z'-LYTE® Assay Controls:
   The following controls are made for each individual kinase and are located on the same plate as the kinase:
0% Phosphorylation Control (100% Inhibition Control)
   The maximum Emission Ratio is established by the 0% Phosphorylation Control (100% Inhibition Control), which contains no ATP and therefore exhibits no kinase activity. This control yields 100% cleaved peptide in the Development Reaction.
100% Phosphorylation Control
   The 100% Phosphorylation Control, which consists of a synthetically phosphorylated peptide of the same sequence as the peptide substrate, is designed to allow for the calculation of percent phosphorylation. This control yields a very low percentage of cleaved peptide in the Development Reaction.

The 0% Phosphorylation and 100% Phosphorylation Controls allow one to calculate the percent Phosphorylation achieved in a specific reaction well. Control wells do not include any kinase inhibitors.

0% Inhibition Control

The minimum Emission Ratio in a screen is established by the 0% Inhibition Control, which contains active kinase. This control is designed to produce a 10-50%* phosphorylated peptide in the Kinase Reaction.

* Cascade assays may produce up to 70% phosphorylated peptide.

Known Inhibitor

A known inhibitor control standard curve, 10 point titration, is run for each individual kinase on the same plate as the kinase to ensure the kinase is inhibited within an expected $IC_{50}$ range previously determined.

The Following Controls are Prepared for Each Concentration of Test Compound Assayed:

Development Reaction Interference

The Development Reaction Interference is established by comparing the Test Compound Control wells that do not contain ATP versus the 0% Phosphorylation Control (which does not contain the Test Compound). The expected value for a non-interfering compound should be 100%. Any value outside of 90% to 110% is flagged.

Test Compound Fluorescence Interference

The Test Compound Fluorescence Interference is determined by comparing the Test Compound Control wells that do not contain the Kinase/Peptide Mixture (zero peptide control) versus the 0% Inhibition Control. The expected value for a non-fluorescence compound should be 0%. Any value>20% is flagged.

Z'-LYTE® Data Analysis:

The following equations are used for each set of data points:

$$\% \text{ Phosphorylation } (\% \text{ Phos}) = \left\{ 1 - \frac{(\text{Emission Ratio} \times F_{100\%}) - C_{100\%}}{(C_{0\%} - C_{100\%}) + [\text{Emission Ratio} \times (F_{100\%} - F_{0\%})]} \right\} * 100$$

$$\% \text{ Inhibition} = \left\{ 1 - \frac{\% \text{ Phos}_{Sample}}{\% \text{ Phos}_{0\% \text{ Inhibition Ctl}}} \right\} * 100$$

$C_{100\%}$ = Average Coumarin emission signal of the 100% *Phos.* Control $C_{0\%}$ = Average Coumarin emission signal of the 0% *Phos.* Control $F_{100\%}$ = Average Fluorescein emission signal of the 100% *Phos.* Control $F_{0\%}$ = Average Fluorescein emission signal of the 0% *Phos.* Control Kinase-Specific Assay Conditions:

ABL1

The 2×ABL1 (# P3049)/Tyr 02 (Z'-LYTE® Kinase Assay Kit—Tyrosine 2 Peptide, # PV 3191) mixture is prepared in 50 mM HEPES pH 7.5, 0.01% BRIJ-35, 10 mM $MgCl_2$, 1 mM EGTA. The final 10 µL Kinase Reaction consists of 0.29-2.52 ng ABL1 and 2 µM Tyr 02 in 50 mM HEPES pH 7.5, 0.01% BRIJ-35, 10 mM $MgCl_2$, 1 mM EGTA. After the 1 hour Kinase Reaction incubation, 5 µL of a 1:128 dilution of Development Reagent A is to added.

ACVR1B (ALK4)

The 2×ACVR1B (ALK4) (# PV4312)/Ser/Thr 16 (Z'-LYTE® Kinase Assay Kit—Ser/Thr 16 Peptide, # PV 3802) mixture is prepared in 50 mM HEPES pH 7.5, 0.01% BRIJ-35, 10 mM $MnCl_2$, 1 mM EGTA, 2 mM DTT, 0.02% $NaN_3$. The final 10 µL Kinase Reaction consists of 9.15-60 ng ACVR1B (ALK4) and 2 µM Ser/Thr 16 in 50 mM HEPES pH 7.5, 0.01% BRIJ-35, 5 mM $MgCl_2$, 5 mM $MnCl_2$, 1 mM EGTA, 1 mM DTT, 0.01% $NaN_3$. After the 1 hour Kinase Reaction incubation, 5 µL of a 1:16 dilution of Development Reagent B is added.

AKT2 (PKB beta)

The 2×AKT2 (PKB beta) (# PV3975)/Ser/Thr 06 (Z'-LYTE® Kinase Assay Kit—Ser/Thr 6 Peptide, # PV 3179) mixture is prepared in 50 mM HEPES pH 7.5, 0.01% BRIJ-35, 10 mM $MgCl_2$, 1 mM EGTA. The final 10 µL Kinase Reaction consists of 0.78-40 ng AKT2 (PKB beta) and 2 µM Ser/Thr 06 in 50 mM HEPES pH 7.5, 0.01% BRIJ-35, 10 mM $MgCl_2$, 1 mM EGTA. After the 1 hour Kinase Reaction incubation, 5 µL of a 1:4096 dilution of Development Reagent A is added.

AMPK A1/B1/G1

The 2×AMPK A1/B1/G1 (# PV 4672)/Ser/Thr 23 (Z'-LYTE® Kinase Assay Kit—Ser/Thr 23 Peptide, # PV 4644) mixture is prepared in 50 mM HEPES pH 7.5, 0.01% BRIJ-35, 10 mM $MgCl_2$, 1 mM EGTA. The final 10 µL Kinase Reaction consists of 0.43-2.86 ng AMPK A1/B1/G1 and 2 µM Ser/Thr 23 in 50 mM HEPES pH 7.5, 0.01% BRIJ-35, 10 mM $MgCl_2$, 1 mM EGTA. After the 1 hour Kinase Reaction incubation, 5 µL of a 1:4096 dilution of Development Reagent A is added.

CAMK1D (CaMKI Delta)

The 2×CAMK1D (CaMKI delta) (# PV 3663)/Ser/Thr 25 (Z'-LYTE® Kinase Assay Kit—Ser/Thr 25 Peptide, # PV 5116) mixture is prepared in 50 mM HEPES pH 6.5. 0.01% BRIJ-35, 10 mM $MgCl_2$, 1 mM EGTA, 4 mM $CaCl_2$, 800 U/mL Calmodulin, 0.02% $NaN_3$. The final 10 µL Kinase Reaction consists of 15.9-133 ng CAMK1D (CaMKI delta) and 2 µM Ser/Thr 25 in 50 mM HEPES pH 7.0, 0.01% BRIJ-35, 10 mM $MgCl_2$, 1 mM EGTA, 2 mM $CaCl_2$, 400 U/mL Calmodulin, 0.01% $NaN_3$. After the 1 hour Kinase Reaction incubation, 5 µL of a 1:4096 dilution of Development Reagent A is added.

CAMK2D (CaMKII Delta)

The 2×CAMK2D (CaMKII delta) (# PV 3373)/Ser/Thr 04 (Z'-LYTE® Kinase Assay Kit—Ser/Thr 4 Peptide, # PV 3177) mixture is prepared in 50 mM HEPES pH 7.5, 0.01% BRIJ-35, 10 mM $MgCl_2$, 1 mM EGTA, 4 mM $CaCl_2$), 800 U/mL Calmodulin, 0.02% $NaN_3$. The final 10 µL Kinase Reaction consists of 0.08-0.74 ng CAMK2D (CaMKII delta) and 2 µM Ser/Thr 04 in 50 mM HEPES pH 7.5, 0.01% BRIJ-35, 10 mM $MgCl_2$, 1 mM EGTA, 2 mM $CaCl_2$), 400 U/mL Calmodulin, 0.01% $NaN_3$. After the 1 hour Kinase Reaction incubation, 5 µL of a 1:1024 dilution of Development Reagent A is added.

CDK2/Cyclin A

The 2×CDK2/cyclin A (# PV 3267)/Ser/Thr 12 (Z'-LYTE® Kinase Assay Kit—Ser/Thr 12 Peptide, # PV 3673) mixture is prepared in 50 mM HEPES pH 7.5, 0.01% BRIJ-35, 10 mM $MgCl_2$, 1 mM EGTA. The final 10 µL Kinase Reaction consists of 1.22-10.3 ng CDK2/cyclin A and 2 µM Ser/Thr 12 in 50 mM HEPES pH 7.5, 0.01% BRIJ-35, 10 mM $MgCl_2$. 1 mM EGTA. After the 1 hour Kinase Reaction incubation, 5 µL of a 1:4096 dilution of Development Reagent A is added.

CHEK1 (CHK1)

The 2×CHEK1 (CHK1) (# P 3040)/Ser/Thr 19 (Z'-LYTE® Kinase Assay Kit—Ser/Thr 19 Peptide, # PV 4529) mixture is prepared in 50 mM HEPES pH 7.5, 0.01% BRIJ-35, 10 mM MgCl$_2$, 1 mM EGTA. The final 10 µL Kinase Reaction consists of 2.04-35 ng CHEK1 (CHK1) and 2 µM Ser/Thr 19 in 50 mM HEPES pH 7.5, 0.01% BRIJ-35, 10 mM MgCl$_2$. 1 mM EGTA. After the 1 hour Kinase Reaction incubation, 5 µL of a 1:256 dilution of Development Reagent A is added.

CSNK1A1 (CK1 alpha 1)

The 2×CSNK1A1 (CK1 alpha 1) (# PV 3850)/Ser/Thr 11 (Z'-LYTE® Kinase Assay Kit—Ser/Thr 11 Peptide, # PV 3670) mixture is prepared in 50 mM HEPES pH 7.5, 0.01% BRIJ-35, 10 mM MgCl$_2$, 1 mM EGTA, 2 mM DTT. The final 10 µL Kinase Reaction consists of 2.6-13.5 ng CSNK1A1 (CK1 alpha 1) and 2 µM Ser/Thr 11 in 50 mM HEPES pH 7.5, 0.01% BRIJ-35, 10 mM MgCl$_2$, 1 mM EGTA, 1 mM DTT. After the 1 hour Kinase Reaction incubation, 5 µL of a 1:16 dilution of Development Reagent B is added.

CSNK2A1 (CK2 alpha 1)

The 2×CSNK2A1 (CK2 alpha 1) (# PV 3248)/Ser/Thr 11 (Z'-LYTE® Kinase Assay Kit—Ser/Thr 11 Peptide, # PV 3670) mixture is prepared in 50 mM HEPES pH 7.5, 0.01% BRIJ-35, 10 mM MgCl$_2$, 1 mM EGTA. The final 10 µL Kinase Reaction consists of 0.68-25.7 ng CSNK2A1 (CK2 alpha 1) and 2 µM Ser/Thr 11 in 50 mM HEPES pH 7.5, 0.01% BRIJ-35, 10 mM MgCl$_2$, 1 mM EGTA. After the 1 hour Kinase Reaction incubation, 5 µL of a 1:16 dilution of Development Reagent B is added.

EGFR (ErbB1)

The 2×EGFR (ErbB1) (# PV 3872)/Tyr 04 (Z'-LYTE® Kinase Assay Kit—Tyrosine 4 Peptide, # PV 3193) mixture is prepared in 50 mM HEPES pH 7.5, 0.01% BRIJ-35, 10 mM MgCl$_2$, 4 mM MnCl$_2$, 1 mM EGTA, 2 mM DTT. The final 10 µL Kinase Reaction consists of 1.1-8 ng EGFR (ErbB1) and 2 µM Tyr 04 in 50 mM HEPES pH 7.5, 0.01% BRIJ-35, 10 mM MgCl$_2$, 2 mM MnCl$_2$, 1 mM EGTA, 1 mM DTT. After the 1 hour Kinase Reaction incubation, 5 µL of a 1:64 dilution of Development Reagent B is added.

EPHB2

The 2×EPHB2 (# PV 3625)/Tyr 02 (Z'-LYTE® Kinase Assay Kit—Tyrosine 2 Peptide, # PV 3191) mixture is prepared in 50 mM HEPES pH 7.5, 0.01% BRIJ-35, 10 mM MgCl$_2$, 1 mM EGTA. The final 10 µL Kinase Reaction consists of 0.55-36 ng EPHB2 and 2 µM Tyr 02 in 50 mM HEPES pH 7.5, 0.01% BRIJ-35, 10 mM MgCl$_2$, 1 mM EGTA. After the 1 hour Kinase Reaction incubation, 5 µL of a 1:128 dilution of Development Reagent A is added.

FGFR1

The 2×FGFR1 (# PV 3146)/Tyr 04 (Z'-LYTE® Kinase Assay Kit—Tyrosine 4 Peptide, # PV 3193) mixture is prepared in 50 mM HEPES pH 7.5, 0.01% BRIJ-35, 10 mM MgCl$_2$, 4 mM MnCl$_2$, 1 mM EGTA, 2 mM DTT. The final 10 µL Kinase Reaction consists of 0.44-2.45 ng FGFR1 and 2 µM Tyr 04 in 50 mM HEPES pH 7.5, 0.01% BRIJ-35, 10 mM MgCl$_2$, 2 mM MnCl$_2$, 1 mM EGTA, 1 mM DTT. After the 1 hour Kinase Reaction incubation, 5 µL of a 1:64 dilution of Development Reagent B is added.

FRAP1 (mTOR)

The 2×FRAP1 (mTOR) (# PR8683B)/Ser/Thr 11 (Z'-LYTE® Kinase Assay Kit—Ser/Thr 11 Peptide, # PV 3670) mixture is prepared in 50 mM HEPES pH 7.5, 0.01% BRIJ-35, 10 mM MnCl$_2$, 1 mM EGTA, 2 mM DTT, 0.02% NaN$_3$. The final 10 µL Kinase Reaction consists of 11.1-56 ng FRAP1 (mTOR) and 2 µM Ser/Thr 11 in 50 mM HEPES pH 7.5, 0.01% BRIJ-35, 5 mM MgCl$_2$, 5 mM MnCl$_2$, 1 mM EGTA, 1 mM DTT, 0.01% NaN$_3$. After the 1 hour Kinase Reaction incubation, 5 µL of a 1:16 dilution of Development Reagent B is added.

GSK3B (GSK3 Beta)

The 2×GSK3B (GSK3 beta) (# PV 3365)/Ser/Thr 09 (Z'-LYTE® Kinase Assay Kit—Ser/Thr 9 Peptide, # PV 3324) mixture is prepared in 50 mM HEPES pH 7.5, 0.01% BRIJ-35, 10 mM MgCl$_2$, 1 mM EGTA. The final 10 µL Kinase Reaction consists of 0.17-0.88 ng GSK3B (GSK3 beta) and 2 µM Ser/Thr 09 in 50 mM HEPES pH 7.5, 0.01% BRIJ-35, 10 mM MgCl$_2$, 1 mM EGTA. After the 1 hour Kinase Reaction incubation, 5 µL of a 1:512 dilution of Development Reagent A is added.

LCK

The 2×LCK (# P 3043)/Tyr 02 (Z'-LYTE® Kinase Assay Kit—Tyrosine 2 Peptide, # PV 3191) mixture is prepared in 50 mM HEPES pH 7.5, 0.01% BRIJ-35, 10 mM MgCl$_2$, 1 mM EGTA. The final 10 µL Kinase Reaction consists of 2.46-50 ng LCK and 2 µM Tyr 02 in 50 mM HEPES pH 7.5, 0.01% BRIJ-35, 10 mM MgCl$_2$, 1 mM EGTA. After the 1 hour Kinase Reaction incubation, 5 µL of a 1:128 dilution of Development Reagent A is added.

MAP2K1 (MEK1)

The 2×MAP2K1 (MEK1) (# PV 3303)/inactive MAPK1 (ERK2) (# PV 3314)/Ser/Thr 03 (Z'-LYTE® Kinase Assay Kit—Ser/Thr 3 Peptide, # PV 3176) mixture is prepared in 50 mM HEPES pH 7.5, 0.01% BRIJ-35, 10 mM MgCl$_2$, 1 mM EGTA. The final 10 µL Kinase Reaction consists of 0.11-0.45 ng MAP2K1 (MEK1), 105 ng inactive MAPK1 (ERK2), and 2 µM Ser/Thr 03 in 50 mM HEPES pH 7.5, 0.01% BRIJ-35, 10 mM MgCl$_2$, 1 mM EGTA. After the 1 hour Kinase Reaction incubation, 5 µL of a 1:1024 dilution of Development Reagent A is added.

MAP3K8 (COT)

The 2×MAP3K8 (COT) (# PV 4313)/inactive MAP2K1 (MEK1) (# P 3093)/inactive MAPK1 (ERK2) (# PV 3314)/Ser/Thr 03 (Z'-LYTE® Kinase Assay Kit—Ser/Thr 3 Peptide, # PV 3176) mixture is prepared in 50 mM HEPES pH 7.5, 0.01% BRIJ-35, 10 mM MgCl$_2$, 1 mM EGTA. The final 10 µL Kinase Reaction consists of 0.55-2.18 ng MAP3K8 (COT), 1×inactive MAP2K1 (MEK1)/inactive MAPK1 (ERK2), and 2 µM Ser/Thr 03 in 50 mM HEPES pH 7.5, 0.01% BRIJ-35, 10 mM MgCl$_2$, 1 mM EGTA. After the 1 hour Kinase Reaction incubation, 5 µL of a 1:1024 dilution of Development Reagent A is added.

MAPK8 (JNK1)

The 2×MAPK8 (JNK1) (# PV 3593)/inactive MAPKAPK2 (# PV 3316)/Ser/Thr 04 (Z'-LYTE® Kinase Assay Kit—Ser/Thr 4 Peptide, # PV 3177) mixture is prepared in 50 mM HEPES pH 7.5, 0.01% BRIJ-35, 10 mM MgCl$_2$, 1 mM EGTA, 2 mM DTT. The final 10 µL Kinase Reaction consists of 2-8 ng MAPK8 (JNK1), 12.5 ng inactive MAPKAPK2, and 2 µM Ser/Thr 04 in 50 mM HEPES pH 7.5, 0.01% BRIJ-35, 10 mM MgCl$_2$, 1 mM EGTA, 1 mM DTT. After the 1 hour Kinase Reaction incubation, 5 µL of a 1:1024 dilution of Development Reagent A is added.

MAPK9 (JNK2)

The 2×MAPK9 (JNK2) (# PV 4018)/inactive MAPKAPK2 (# PV 3316)/Ser/Thr 04 (Z'-LYTE® Kinase Assay Kit—Ser/Thr 4 Peptide, # PV 3177) mixture is prepared in 50 mM HEPES pH 7.5, 0.01% BRIJ-35, 10 mM MgCl$_2$, 1 mM EGTA, 2 mM DTT. The final 10 µL Kinase Reaction consists of 1.11-4.44 ng MAPK9 (JNK2), 12.5 ng inactive MAPKAPK2, and 2 µM Ser/Thr 04 in 50 mM HEPES pH 7.5, 0.01% BRIJ-35, 10 mM MgCl$_2$, 1 mM EGTA, 1 mM DTT. After the 1 hour Kinase Reaction incubation, 5 μL of a 1:1024 dilution of Development Reagent A is added.

MAPK14 (p38 Alpha)

The 2×MAPK14 (p38 alpha) (# PV 3304)/inactive MAPKAPK2 (# PV 3316)/Ser/Thr 04 (Z'-LYTE® Kinase Assay Kit—Ser/Thr 4 Peptide, # PV 3177) mixture is prepared in 50 mM HEPES pH 7.5, 0.01% BRIJ-35, 10 mM MgCl$_2$, 1 mM EGTA. The final 10 μL Kinase Reaction consists of 0.004-0.02 ng MAPK14 (p38 alpha), 6.5 ng inactive MAPKAPK2, and 2 μM Ser/Thr 04 in 50 mM HEPES pH 7.5, 0.01% BRIJ-35, 10 mM MgCl$_2$, 1 mM EGTA. After the 1 hour Kinase Reaction incubation, 5 μL of a 1:1024 dilution of Development Reagent A is added.

MAPKAPK2

The 2×MAPKAPK2 (# PV 3317)/Ser/Thr 04 (Z'-LYTE® Kinase Assay Kit—Ser/Thr 4 Peptide, # PV 3177) mixture is prepared in 50 mM HEPES pH 7.5, 0.01% BRIJ-35, 10 mM MgCl$_2$, 1 mM EGTA. The final 10 μL Kinase Reaction consists of 0.04-0.18 ng MAPKAPK2 and 2 μM Ser/Thr 04 in 50 mM HEPES pH 7.5, 0.01% BRIJ-35, 10 mM MgCl$_2$, 1 mM EGTA. After the 1 hour Kinase Reaction incubation, 5 μL of a 1:1024 dilution of Development Reagent A is added.

MYLK2 (skMLCK)

The 2×MYLK2 (skMLCK) (# PV 3757)/Ser/Thr 13 (Z'-LYTE® Kinase Assay Kit—Ser/Thr 13 Peptide, # PV 3793) mixture is prepared in 50 mM HEPES pH 7.5, 0.01% BRIJ-35, 10 mM MgCl$_2$, 1 mM EGTA, 4 mM CaCl$_2$, 800 U/mL Calmodulin, 0.02% NaN$_3$. The final 10 μL Kinase Reaction consists of 6.71-48.9 ng MYLK2 (skMLCK) and 2 μM Ser/Thr 13 in 50 mM HEPES pH 7.5, 0.01% BRIJ-35, 10 mM MgCl$_2$, 1 mM EGTA, 2 mM CaCl$_2$, 400 U/mL Calmodulin, 0.01% NaN$_3$. After the 1 hour Kinase Reaction incubation, 5 μL of a 1:1024 dilution of Development Reagent A is added.

NEK2

The 2×NEK2 (# PV 3360)/Ser/Thr 07 (Z'-LYTE® Kinase Assay Kit—Ser/Thr 7 Peptide, # PV 3180) mixture is prepared in 50 mM HEPES pH 7.5, 0.01% BRIJ-35, 10 mM MgCl$_2$, 1 mM EGTA. The final 10 μL Kinase Reaction consists of 0.5-5.4 ng NEK2 and 2 μM Ser/Thr 07 in 50 mM HEPES pH 7.5, 0.01% BRIJ-35, 10 mM MgCl$_2$, 1 mM EGTA. After the 1 hour Kinase Reaction incubation, 5 μL of a 1:65000 dilution of Development Reagent A is added.

PAK4

The 2×PAK4 (# PV 4212)/Ser/Thr 20 (Z'-LYTE® Kinase Assay Kit—Ser/Thr 20 Peptide, # PV 4532) mixture is prepared in 50 mM HEPES pH 7.5, 0.01% BRIJ-35, 10 mM MgCl$_2$, 1 mM EGTA. The final 10 μL Kinase Reaction consists of 0.1-0.75 ng PAK4 and 2 μM Ser/Thr 20 in 50 mM HEPES pH 7.5, 0.01% BRIJ-35, 10 mM MgCl$_2$, 1 mM EGTA. After the 1 hour Kinase Reaction incubation, 5 μL of a 1:512 dilution of Development Reagent A is added.

PDK1 Direct

The 2×PDK1 Direct/Ser/Thr 07 (Z'-LYTE® Kinase Assay Kit—Ser/Thr 7 Peptide, # PV 3180) mixture is prepared in 50 mM Tris pH 8.5, 0.01% BRIJ-35, 10 mM MgCl$_2$, 1 mM EGTA, 0.02% NaN$_3$. The final 10 μL Kinase Reaction consists of 5.04-29.4 ng PDK1 Direct and 2 μM Ser/Thr 07 in 50 mM Tris/HEPES pH 8.0, 0.01% BRIJ-35, 10 mM MgCl$_2$, 1 mM EGTA, 0.01% NaN$_3$. After the 1 hour Kinase Reaction incubation, 5 μL of a 1:65000 dilution of Development Reagent A is added.

PRKACA (PKA)

The 2×PRKACA (PKA) (# P 2912)/Ser/Thr 01 (Z'-LYTE® Kinase Assay Kit—Ser/Thr 1 Peptide, # PV 3174) mixture is prepared in 50 mM HEPES pH 7.5, 0.01% BRIJ-35, 10 mM MgCl$_2$, 1 mM EGTA. The final 10 μL Kinase Reaction consists of 0.03-0.15 ng PRKACA (PKA) and 2 μM Ser/Thr 01 in 50 mM HEPES pH 7.5, 0.01% BRIJ-35, 10 mM MgCl$_2$, 1 mM EGTA. After the 1 hour Kinase Reaction incubation, 5 μL of a 1:4096 dilution of Development Reagent A is added.

RAF1 (cRAF) Y340D Y341D

The 2×RAF1 (cRAF) Y340D Y341D (# PV 4046)/inactive MAP2K1 (MEK1) (# P 3093)/inactive MAPK1 (ERK2) (# PV 3314)/Ser/Thr 03 (Z'-LYTE® Kinase Assay Kit—Ser/Thr 3 Peptide, # PV 3176) mixture is prepared in 50 mM HEPES pH 7.5, 0.01% BRIJ-35, 10 mM MgCl$_2$, 1 mM EGTA. The final 10 μL Kinase Reaction consists of 0.003-0.01 ng RAF1 (cRAF) Y340D Y341D, 1×inactive MAP2K1 (MEK1)/inactive MAPK1 (ERK2), and 2 μM Ser/Thr 03 in 50 mM HEPES pH 7.5, 0.01% BRIJ-35, 10 mM MgCl$_2$, 1 mM EGTA. After the 1 hour Kinase Reaction incubation, 5 μL of a 1:1024 dilution of Development Reagent A is added.

ROCK2

The 2×ROCK2 (# PV 3759)/Ser/Thr 13 (Z'-LYTE® Kinase Assay Kit—Ser/Thr 13 Peptide, # PV 3793) mixture is prepared in 50 mM HEPES pH 7.5, 0.01% BRIJ-35, 10 mM MgCl$_2$. 1 mM EGTA. The final 10 μL Kinase Reaction consists of 0.62-4.13 ng ROCK2 and 2 μM Ser/Thr 13 in 50 mM HEPES pH 7.5, 0.01% BRIJ-35, 10 mM MgCl$_2$, 1 mM EGTA. After the 1 hour Kinase Reaction incubation, 5 μL of a 1:1024 dilution of Development Reagent A is added.

SRPK2

The 2×SRPK2 (# PV 3829)/Ser/Thr 07 (Z'-LYTE® Kinase Assay Kit—Ser/Thr 7 Peptide, # PV 3180) mixture is prepared in 50 mM HEPES pH 7.5, 0.01% BRIJ-35, 10 mM MgCl$_2$, 1 mM EGTA. The final 10 μL Kinase Reaction consists of 3.76-52 ng SRPK2 and 2 μM Ser/Thr 07 in 50 mM HEPES pH 7.5, 0.01% BRIJ-35, 10 mM MgCl$_2$, 1 mM EGTA. After the 1 hour Kinase Reaction incubation, 5 μL of a 1:65000 dilution of Development Reagent A is added.

STK3 (MST2)

The 2×STK3 (MST2) (# PV 4805)/Ser/Thr 07 (Z'-LYTE® Kinase Assay Kit—Ser/Thr 7 Peptide, # PV 3180) mixture is prepared in 50 mM HEPES pH 6.5, 0.01% BRIJ-35, 10 mM MgCl$_2$, 1 mM EGTA, 0.02% NaN$_3$. The final 10 μL Kinase Reaction consists of 6.25-38.7 ng STK3 (MST2) and 2 μM Ser/Thr 07 in 50 mM HEPES pH 7.0, 0.01% BRIJ-35, 10 mM MgCl$_2$, 1 mM EGTA, 0.01% NaN$_3$. After the 1 hour Kinase Reaction incubation, 5 μL of a 1:65000 dilution of Development Reagent A is added.

STK6 (AURKA (Aurora A))

The 2×AURKA (Aurora A) (# PV 3612)/Ser/Thr 01 (Z'-LYTE® Kinase Assay Kit—Ser/Thr 1 Peptide, # PV 3174) mixture is prepared in 50 mM HEPES pH 7.5, 0.01% BRIJ-35, 10 mM MgCl$_2$, 1 mM EGTA. The final 10 μL Kinase Reaction consists of 0.91-12.2 ng AURKA (Aurora A) and 2 μM Ser/Thr 01 in 50 mM HEPES pH 7.5, 0.01% BRIJ-35, 10 mM MgCl$_2$, 1 mM EGTA. After the 1 hour Kinase Reaction incubation, 5 μL of a 1:4096 dilution of Development Reagent A is added.

TBK1

The 2×TBK1 (# PV 3504)/Ser/Thr 05 (Z'-LYTE® Kinase Assay Kit—Ser/Thr 5 Peptide, # PV 3178) mixture is prepared in 50 mM HEPES pH 7.5, 0.01% BRIJ-35, 10 mM MgCl$_2$, 1 mM EGTA. The final 10 μL Kinase Reaction consists of 0.7-9.72 ng TBK1 and 2 μM Ser/Thr 05 in 50 mM HEPES pH 7.5, 0.01% BRIJ-35, 10 mM MgCl$_2$, 1 mM EGTA. After the 1 hour Kinase Reaction incubation, 5 μL of a 1:64 dilution of Development Reagent B is added.

Table 8 shows the % inhibition values of example compounds and prior art compounds determined using the profiling service described hereinbefore.

TABLE 8

|  | I-1 | I-2 | I-3 |
|---|---|---|---|
|  | # kinases inhibited >50% @ 1 μM (printed in bold below) | | |
|  | 6/30 | 7/30 | 6/30 |
| ABL1 [%] | 24 | 17 | 27 |
| ACVR1B [%] | −10 | 0 | 0 |
| AKT2 [%] | 3 | 1 | 7 |
| AMPK A1B1G1 [%] | 36 | 34 | 43 |
| CDK2/CYCLINA [%] | 72 | 56 | 66 |
| CHEK1 [%] | 11 | 23 | 31 |
| CSNK1A1 [%] | 16 | 49 | 37 |
| CSNK2A1 [%] | 4 | 10 | 3 |
| EGFR [%] | 65 | 68 | 72 |
| EPHB2 [%] | 64 | 68 | 77 |
| FGFR1 [%] | 30 | 40 | 34 |
| FRAP1 (MTOR) [%] | −6 | 1 | −10 |
| GSK3B [%] | 14 | 10 | 9 |
| LCK [%] | 85 | 78 | 82 |
| MAP2K1 [%] | 34 | 58 | 50 |
| MAP3K8 [%] | 27 | 57 | 45 |
| MAPK14[%] | −5 | 7 | 2 |
| MAPKAPK2 [%] | −3 | 1 | 2 |
| MYLK2 [%] | 16 | 3 | 12 |
| NEK2 [%] | 15 | 25 | 29 |
| PAK4 [%] | 14 | 24 | 39 |
| PDK1 [%] | −2 | 1 | 9 |
| PRKACA [%] | −5 | 22 | 13 |
| RAF1 [%] | 16 | 40 | 31 |
| ROCK2 [%] | 1 | 6 | 7 |
| CAMK2D [%] | 53 | 47 | 58 |
| SRPK2 [%] | 58 | 79 | 49 |
| STK3 [%] | 1 | 5 | −1 |
| STK6 (Aur A) [%] | −15 | 12 | 14 |
| TBK1 [%] | 38 | 48 | 51 |
| MAPK8 [%] | n.a. | n.a. | n.a. |
| MAPK9 [%] | n.a. | n.a. | n.a. |

|  | I-7 | I-8 | I-9 |
|---|---|---|---|
|  | # kinases inhibited >50% @ 1 μM (printed in bold below) | | |
|  | 6/30 | 3/30 | 6/30 |
| ABL1 [%] | 22 | 10 | 17 |
| ACVR1B [%] | 0 | −4 | 7 |
| AKT2 [%] | 7 | 4 | 2 |
| AMPK A1B1G1 [%] | 39 | 29 | 35 |
| CDK2/CYCLINA [%] | 74 | 49 | 63 |
| CHEK1 [%] | 38 | 17 | 26 |
| CSNK1A1 [%] | 29 | 38 | 37 |
| CSNK2A1 [%] | 8 | 7 | 1 |
| EGFR [%] | 77 | 56 | 65 |
| EPHB2 [%] | 82 | 62 | 73 |
| FGFR1 [%] | 34 | 29 | 32 |
| FRAP1 (MTOR) [%] | 3 | −8 | −12 |
| GSK3B [%] | 10 | 14 | 9 |
| LCK [%] | 84 | 59 | 80 |
| MAP2K1 [%] | 40 | 48 | 36 |
| MAP3K8 [%] | 42 | 38 | 37 |
| MAPK14 [%] | 2 | −5 | 4 |
| MAPKAPK2 [%] | 5 | 5 | 3 |
| MYLK2 [%] | 23 | 13 | 10 |
| NEK2 [%] | 32 | 22 | 32 |
| PAK4 [%] | 19 | 21 | 32 |
| PDK1 [%] | 3 | 5 | 6 |
| PRKACA [%] | 16 | 16 | 17 |
| RAF1 [%] | 36 | 25 | 32 |
| ROCK2 [%] | 9 | 7 | 3 |
| CAMK2D [%] | 64 | 40 | 69 |
| SRPK2 [%] | 58 | 48 | 49 |
| STK3 [%] | 15 | −1 | −15 |
| STK6 (Aur A) [%] | 5 | 6 | 10 |
| TBK1 [%] | 49 | 46 | 57 |

TABLE 8-continued

|  |  |  |  |
|---|---|---|---|
| MAPK8 [%] | n.a. | n.a. | n.a. |
| MAPK9 [%] | n.a. | n.a. | n.a. |

|  | I-11 | I-166 in WO 2012/010704 | I-167 in WO 2012/010704 |
|---|---|---|---|
|  | # kinases inhibited >50% @ 1 μM (printed in bold below) | | |
|  | 4/30 | 13/30 | 12/30 |
| ABL1 [%] | 10 | 44 | 24 |
| ACVR1B [%] | −11 | −14 | −16 |
| AKT2 [%] | 3 | 7 | 8 |
| AMPK A1B1G1 [%] | 28 | 62 | 52 |
| CDK2/CYCLINA [%] | 53 | 84 | 77 |
| CHEK1 [%] | 25 | 34 | 28 |
| CSNK1A1 [%] | 17 | 14 | 11 |
| CSNK2A1 [%] | 2 | 27 | 29 |
| EGFR [%] | 53 | 74 | 55 |
| EPHB2 [%] | 56 | 77 | 72 |
| FGFR1 [%] | 28 | 59 | 50 |
| FRAP1 (MTOR) [%] | −11 | 15 | 6 |
| GSK3B [%] | 8 | 32 | 33 |
| LCK [%] | 76 | 89 | 86 |
| MAP2K1 [%] | 39 | 96 | 93 |
| MAP3K8 [%] | 22 | 81 | 78 |
| MAPK14 [%] | 1 | 46 | 11 |
| MAPKAPK2 [%] | −2 | 12 | 9 |
| MYLK2 [%] | 16 | 48 | 36 |
| NEK2 [%] | 24 | 18 | 11 |
| PAK4 [%] | 27 | 60 | 61 |
| PDK1 [%] | 20 | 20 | 17 |
| PRKACA [%] | −3 | 17 | 18 |
| RAF1 [%] | 14 | 92 | 90 |
| ROCK2 [%] | 9 | −11 | −18 |
| CAMK2D [%] | 38 | 59 | 55 |
| SRPK2 [%] | 38 | 11 | 7 |
| STK3 [%] | −2 | −4 | −15 |
| STK6 (Aur A) [%] | −12 | 72 | 76 |
| TBK1 [%] | 33 | 81 | 78 |
| MAPK8 [%] | 12 | n.a. | 61 |
| MAPK9 [%] | 7 | n.a. | 59 |

In summary, the compounds (I) according to the invention have the following profile:

High inhibitory activity on IGF-1R (<10 nM);
High potency on cancer cells dependent on IGF-1R signalling for proliferation, exemplified on TC71 (<10 nM)
Tailored pharmacokinetic properties to mitigate the risk of complications arising from prolonged hyperglycemia;
High selectivity for IGF-1R.

No structurally similar prior art compounds are known to share this beneficial properties with compounds (I).

On the basis of their biological properties the compounds of formula (I) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers/proliferative diseases may be treated with compounds according to the invention, without being restricted thereto:
brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder and other urothelial cancers; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma, hormone receptor positive breast cancer (estrogen receptor positive breast cancer, progesterone receptor positive breast cancer), Her2 positive breast cancer, triple negative breast cancer; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, soft tissue sarcoma, liposarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypemephroma or Grawitz's tumour; oesophageal cancer or carcinoma of the oesophagus; penile cancer; prostate cancer (e.g. castration-resistant prostate cancer); throat cancer or carcinomas of the pharynx such as for example nasopharynx carcinomas, oropharynx carcinomas and hypopharynx carcinomas; retinoblastoma, vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of formula (I) may be used on their own or in combination with other active substances according to the invention, optionally also in combination with other pharmacologically active substances.

Therapeutic agents which may be administered in combination with the compounds according to the invention, include, without being restricted thereto, hormones, hormone analogues and antihormones, aromatase inhibitors, LHRH agonists and antagonists, inhibitors of growth factors and growth factor receptors (growth factors such as for example "platelet derived growth factor (PDGF)", "fibroblast growth factor (FGF)", "vascular endothelial growth factor (VEGF)", "epidermal growth factor (EGF)", "insulin-like growth factors (IGF)", "human epidermal growth factor (HER, e.g. HER2, HER3, HER4)" and "hepatocyte growth factor (HGF)"; inhibitors are for example "growth factor" antibodies, "growth factor receptor" antibodies and receptor tyrosine kinase inhibitors), antimetabolites (e.g. antifolates), pyrimidine analogues, purine and adenosine analogues, anti-tumour antibiotics (e.g. anthracyclins), platinum derivatives, alkylation agents, nitrosoureas, antimitotic agents (e.g. Vinca alkaloids) and taxanes, tubuline inhibitors; PARP inhibitors, topoisomerase inhibitors (e.g. epipodophyllotoxins), serine/threonine kinase inhibitors (e.g. PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), receptor tyrosine kinase (RTK) inhibitors, protein protein interaction inhibitors (e.g. IAP, Mcl-1, MDM2/MDMX), MEK inhibitors, ERK inhibitors. IGF-1R inhibitors, ErbB receptor inhibitors, rapamycin analogs, androgen synthesis inhibitors, androgen receptor inhibitors, immunotherapy, radiopharmaceuticals, immunotherapeutic agents, conjugated oestrogens, OX44 antibodies, 4-1BB antibodies. PD-1 antibodies and various chemotherapeutic agents and cytotoxics.

IGF-1R/IR inhibitors potentially influence blood glucose level as a side effect (e.g. hyperglycemia, see WO 2005/034868). Thus, it is one aspect of the invention to use an IGF-IR/IR inhibitor (I) in combination with an anti-diabetic drug.

Suitable preparations include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc, agents for delaying release, such as carboxymethyl cellulose, cellulose acetate phthalate, or polyvinyl acetate, carriers, adjuvants, surfactants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 50 to 1000 mg, more preferably from 100 to 500 mg.

The dosage for intravenous use is from 1 mg to 1000 mg per hour, preferably between 5 mg and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of pharmaceutical formulations

| | Tablets | per tablet |
|---|---|---|
| A) | active substance according to formulae (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| | Tablets | per tablet |
|---|---|---|
| B) | active substance according to formulae (I) | 80 mg |
| | lactose | 55 mg |
| | corn starch | 190 mg |
| | microcrystalline cellulose | 35 mg |
| | polyvinylpyrrolidone | 15 mg |

| Tablets | per tablet |
| --- | --- |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| | Ampoule solution | |
| --- | --- | --- |
| C) | active substance according to formulae (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of formula (I):

or a pharmaceutically acceptable salt thereof, wherein:
ring A is a 5-7 membered nitrogen-containing heterocyclyl, optionally substituted by an oxo group;
each R is independently $C_{1-6}$alkyl, optionally substituted by one or more substituents independently selected from the group consisting of $R^{b1}$ and $R^{c1}$;
each $R^{b1}$ is independently selected from the group consisting of $—OR^{c1}$ and $—C(O)OR^{c1}$;
each $R^{c1}$ is independently selected from the group consisting of hydrogen, 3-10 membered heterocyclyl and $C_{1-6}$ alkyl, wherein the $C_{1-6}$alkyl is optionally substituted by a 3-10 membered heterocyclyl; and q is 0, 1 or 2.

2. The compound according to claim 1, or a pharmaceutically acceptable salt thereof, wherein:
ring A is selected from the group consisting of pyrrolidinyl, piperidinyl, piperazinyl, morpholinyl, azepanyl, 1,4-diazepanyl and 1,4-oxazepanyl, each optionally substituted by an oxo group.

3. The compound according to claim 2, or a pharmaceutically acceptable salt thereof, wherein:
ring A is selected from the group consisting of piperazinyl, piperazinonyl and morpholinyl.

4. The compound according to claim 3, or a pharmaceutically acceptable salt thereof, wherein:
ring A is selected from the group consisting of piperazin-1-yl, 2-oxopiperazin-4-yl and morpholin-4-yl.

5. The compound according to claim 4, or a pharmaceutically acceptable salt thereof, wherein:
ring A is piperazin-1-yl.

6. The compound according to claim 5, or a pharmaceutically acceptable salt thereof, wherein:
ring A is piperazin-1-yl; and
q is 0, 1 or 2;
with the proviso that if q is 1 or 2, at least one R is bonded to the 4-position of the piperazin-1-yl.

7. The compound according to claim 1, or a pharmaceutically acceptable salt thereof, wherein:
each R is independently $C_{1-6}$alkyl, optionally substituted by $—OH$ or $—OCH_3$.

8. The compound according to claim 1, or a pharmaceutically acceptable salt thereof, wherein:
each R is independently selected from the group consisting of $CH_3$ and $CH_2CH_3$, wherein each $CH_3$ and $CH_2CH_3$ is independently substituted by a substituent independently selected from the group consisting of $—C(O)OR^{c1}$ and 5-6 membered heterocyclyl; and
each $R^{c1}$ is independently selected from the group consisting of 5-6 membered heterocyclyl and $CH_3$, wherein the $CH_3$ is substituted by a 5-6 membered heterocyclyl.

9. The compound according to claim 8, or a pharmaceutically acceptable salt thereof, wherein:
each R is independently substituted by a substituent selected from the group consisting of pyrrolidinyl, tetrahydrofuryl and tetrahydropyranyl.

10. The compound according to claim 1, or a pharmaceutically acceptable salt thereof, wherein:
q is 1.

11. The compound according to claim 10, or a pharmaceutically acceptable salt thereof, wherein:
R is bonded to a nitrogen atom of ring A.

12. The compound according to claim 1, or a pharmaceutically acceptable salt thereof, wherein:
q is 0.

13. The compound according to claim 1, wherein the compound is selected from the group consisting of:

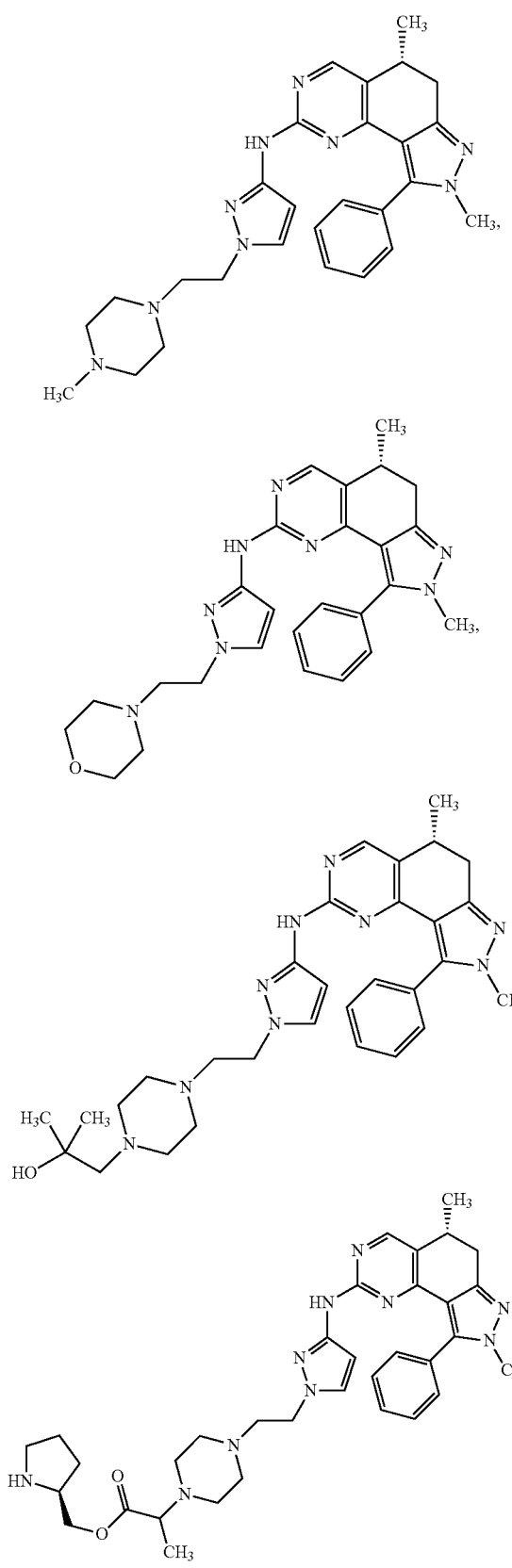
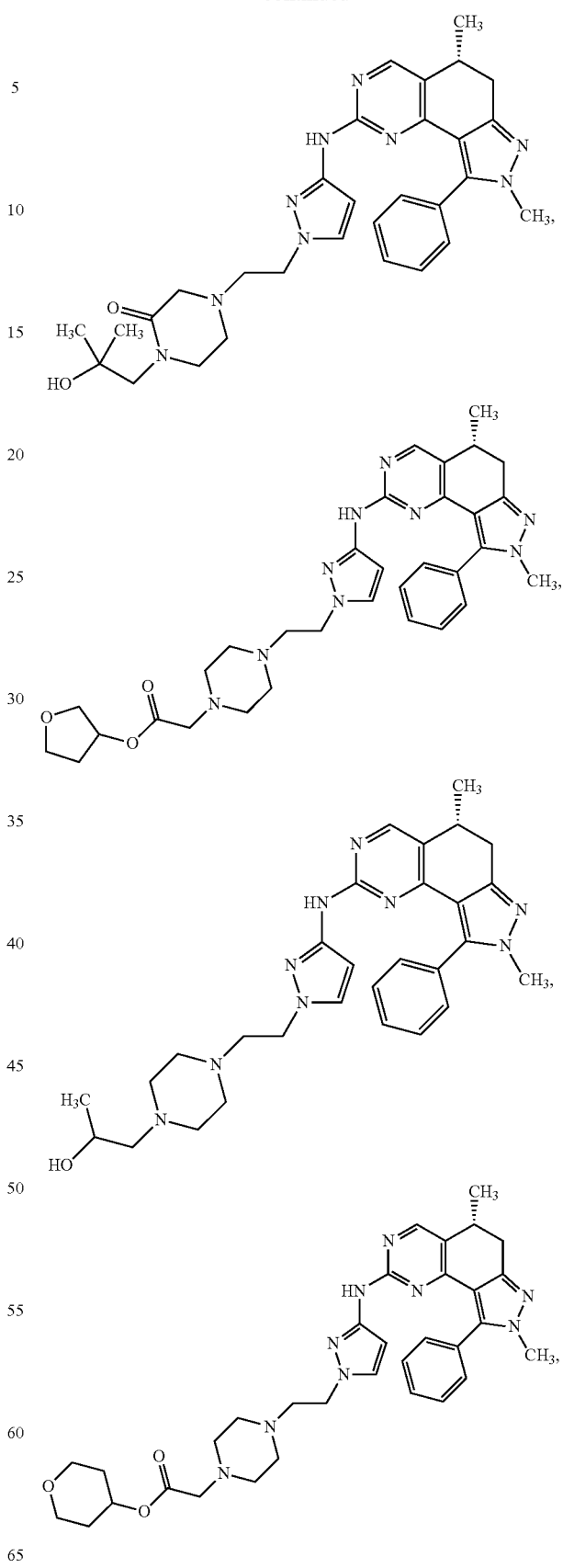

-continued

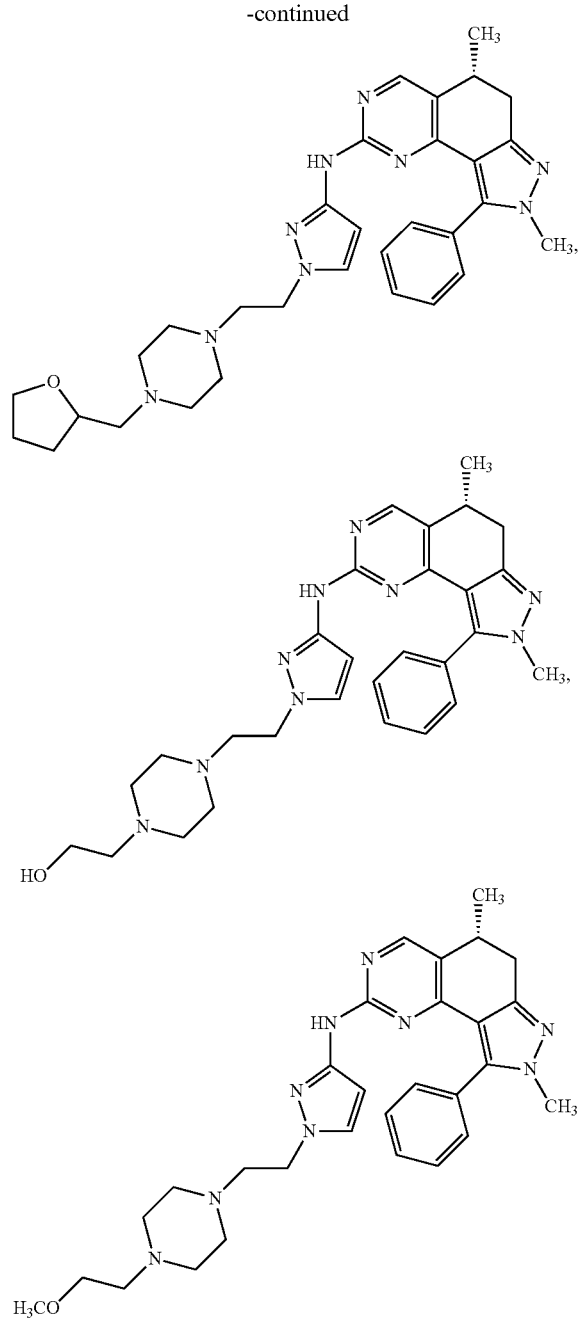

-continued
and

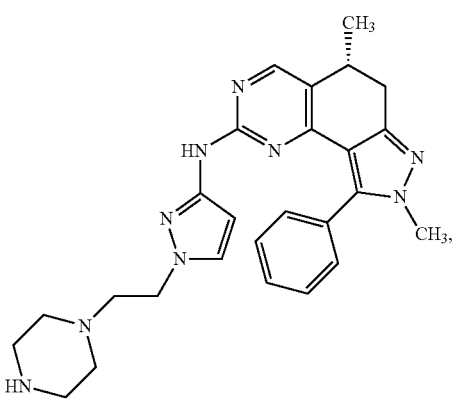

or a pharmaceutically acceptable salt thereof.

14. A pharmaceutical composition comprising at least one compound according to claim 1, or a pharmaceutically acceptable salt thereof, and a pharmaceutically acceptable carrier.

15. The pharmaceutical composition according to claim 14, wherein the pharmaceutical composition further comprises one or more additional cytostatic or cytotoxic active substances.

16. A method for inhibiting insulin-like growth factor-1 receptor activity or insulin receptor activity in a subject, comprising administering to the subject in need thereof a therapeutically effective amount of a compound according to claim 1, or a pharmaceutically acceptable salt thereof.

17. The method according to claim 16, wherein the subject has a disease or condition wherein the inhibition of insulin-like growth factor-1 or insulin receptor is of therapeutic benefit selected from the group consisting of a solid tumor, a viral infection, a bacterial infection, a fungal infection, a parasitic infection, an inflammatory disease, an autoimmune disease, a bone disease, a skin disease, a cardiovascular disease, a disease based on hyperplasia which is characterized by an increase in the number of cells, and cancer.

18. The method according to claim 17, wherein the cancer is intrinsically dependent on oncogenic signaling via the insulin-like growth factor-1 receptor and/or insulin receptor.

* * * * *